(12) United States Patent
Call

(10) Patent No.: US 7,799,567 B1
(45) Date of Patent: *Sep. 21, 2010

(54) AIR SAMPLER BASED ON VIRTUAL IMPACTION AND ACTUAL IMPACTION

(75) Inventor: Charles J. Call, Albuquerque, NM (US)

(73) Assignee: MesoSystems Technology, Inc., Albuquerque, NM (US)

( * ) Notice: Subject to any disclaimer, the term of this patent is extended or adjusted under 35 U.S.C. 154(b) by 1097 days.

This patent is subject to a terminal disclaimer.

(21) Appl. No.: 11/458,364

(22) Filed: Jul. 18, 2006

Related U.S. Application Data

(63) Continuation-in-part of application No. 11/385,326, filed on Mar. 21, 2006, which is a continuation-in-part of application No. 11/058,442, filed on Feb. 15, 2005, which is a continuation-in-part of application No. 10/366,595, filed on Feb. 11, 2003, now Pat. No. 6,938,777, and a continuation-in-part of application No. 09/955,481, filed on Sep. 17, 2001, now Pat. No. 6,695,146, said application No. 11/058,442 is a continuation of application No. 10/066,404, filed on Feb. 1, 2002, now Pat. No. 6,887,710, and a continuation of application No. 09/775,872, filed on Feb. 1, 2001, now Pat. No. 6,729,196, which is a continuation of application No. 09/265,619, filed on Mar. 10, 1999, now Pat. No. 6,267,016, and a continuation of application No. 09/265,620, filed on Mar. 10, 1999, now Pat. No. 6,363,800.

(60) Provisional application No. 60/700,228, filed on Jul. 18, 2005, provisional application No. 60/355,915, filed on Feb. 11, 2002, provisional application No. 60/337,674, filed on Nov. 13, 2001.

(51) Int. Cl.
*G01N 1/14* (2006.01)
*G01N 33/00* (2006.01)

(52) U.S. Cl. .................. 436/53; 436/174; 73/28.05; 73/863.22

(58) Field of Classification Search .............. 436/53, 436/174; 422/83, 88; 73/28.05, 863.22
See application file for complete search history.

(56) References Cited

U.S. PATENT DOCUMENTS 3,001,914 A    9/1961   Andersen .................. 435/30

(Continued)

FOREIGN PATENT DOCUMENTS

DE         1310193         9/1934

(Continued)

OTHER PUBLICATIONS

Carrano, John. "*Ultraviolet Light.*" Spie's Oe magazine, Jun. 2003, pp. 20-23.

(Continued)

*Primary Examiner*—Lyle A Alexander
(74) *Attorney, Agent, or Firm*—Ronald M. Anderson

(57) ABSTRACT

Particles are removed from a fluid stream, such as air, and are deposited on one or more collection surfaces. A pre-filter can be employed to reject oversized particles and contaminants, such as rain and insects. A concentrator is employed to increase a concentration of particles larger than a pre-defined particle size in at least a portion of the fluid, producing a concentrated volume of fluid. The concentrator and pre-filter can, for example, be virtual impactors. The concentrated volume of fluid/air is directed to the collection surface(s), where particles in the concentrated volume of air are deposited. In at least one embodiment, the collection surface is a bed of beads, reducing loss of particles that might occur due to particles bouncing from a single collection surface. A sampling component removes a portion of the deposited particles to generate a sample, which is analyzed by an analytical component.

17 Claims, 13 Drawing Sheets

U.S. PATENT DOCUMENTS

| | | | |
|---|---|---|---|
| 3,518,815 A | 7/1970 | McFarland et al | 73/863.22 |
| 3,633,405 A | 1/1972 | Noll | |
| 3,760,630 A | 9/1973 | Brumbaugh | 73/28.05 |
| 3,901,798 A | 8/1975 | Peterson | 209/143 |
| 3,922,905 A | 12/1975 | Roth | 73/28.04 |
| 3,972,226 A | 8/1976 | Rountree et al. | |
| 3,997,297 A | 12/1976 | Jenkins et al. | 23/232 E |
| 4,111,049 A | 9/1978 | Lerner et al. | 73/421.5 R |
| 4,301,002 A | 11/1981 | Loo | 209/143 |
| 4,473,384 A | 9/1984 | Lefkowitz | 55/290 |
| 4,580,440 A | 4/1986 | Reid et al. | 73/23 |
| 4,670,135 A | 6/1987 | Marple et al. | 209/143 |
| 4,689,052 A * | 8/1987 | Ogren et al. | 95/291 |
| 4,697,462 A | 10/1987 | Daube, Jr. et al. | |
| 4,764,186 A | 8/1988 | Langer | |
| 4,767,524 A | 8/1988 | Yeh et al. | 209/143 |
| 4,820,920 A | 4/1989 | Bather | 250/282 |
| 4,941,899 A | 7/1990 | Liu | |
| 4,942,297 A | 7/1990 | Johnson et al. | |
| 4,961,966 A | 10/1990 | Stevens et al. | 427/299 |
| 4,990,740 A | 2/1991 | Meyer | |
| 5,039,490 A | 8/1991 | Marsoner et al. | |
| 5,040,424 A | 8/1991 | Marple et al. | |
| 5,063,164 A | 11/1991 | Goldstein | |
| 5,128,539 A | 7/1992 | Rodgers et al. | |
| 5,254,861 A | 10/1993 | Carpenter et al. | |
| 5,299,141 A | 3/1994 | Hungerford et al. | 364/510 |
| 5,304,125 A | 4/1994 | Leith | 604/57 |
| 5,412,975 A | 5/1995 | Raabe et al. | |
| 5,425,263 A * | 6/1995 | Davies et al. | 73/28.05 |
| 5,425,802 A | 6/1995 | Burton et al. | |
| 5,472,645 A | 12/1995 | Rock et al. | |
| 5,498,271 A | 3/1996 | Marple et al. | |
| 5,512,216 A | 4/1996 | Rock et al. | |
| 5,533,406 A | 7/1996 | Geise | 73/863.22 |
| 5,553,795 A | 9/1996 | Tsai et al. | |
| 5,585,575 A | 12/1996 | Corrigan et al. | 73/863.71 |
| 5,760,314 A | 6/1998 | Bromberg et al. | 73/863.21 |
| 5,776,754 A | 7/1998 | Caldwell | 435/240.2 |
| 5,786,894 A | 7/1998 | Shields et al. | 356/338 |
| 5,932,795 A | 8/1999 | Koutrakis et al. | 73/28.01 |
| 5,949,001 A | 9/1999 | Willeke | 73/865.5 |
| 6,024,923 A | 2/2000 | Melendez et al. | |
| 6,062,392 A | 5/2000 | Birmingham et al. | 209/143 |
| 6,101,886 A | 8/2000 | Brenizer et al. | 73/863.23 |
| 6,110,247 A | 8/2000 | Birmingham et al. | 55/442 |
| 6,125,845 A | 10/2000 | Halvorsen et al. | 128/200.24 |
| 6,194,731 B1 | 2/2001 | Jeys et al. | 250/461.2 |
| 6,217,636 B1 | 4/2001 | McFarland | 95/216 |
| 6,235,002 B1 | 5/2001 | Carver et al. | 604/183 |
| 6,240,768 B1 | 6/2001 | Lemmonier | 73/28.05 |
| 6,267,016 B1 | 7/2001 | Call et al. | |
| 6,276,016 B1 | 8/2001 | Springer | 14/71.1 |
| 6,284,025 B1 | 9/2001 | Kreisberg et al. | 95/267 |
| 6,324,927 B1 | 12/2001 | Ornath et al. | 73/863.11 |
| 6,334,365 B1 | 1/2002 | Linker et al. | 73/864.81 |
| 6,363,800 B1 | 4/2002 | Call et al. | |
| 6,386,015 B1 | 5/2002 | Rader et al. | 73/31.05 |
| 6,435,043 B1 | 8/2002 | Ferguson et al. | 73/863.22 |
| 6,573,836 B1 | 6/2003 | Gitis et al. | 340/603 |
| 6,695,146 B2 | 2/2004 | Call et al. | 73/863.22 |
| 6,707,539 B2 | 3/2004 | Selinfreund et al. | |
| 7,096,125 B2 | 8/2006 | Padmanabhan et al. | 702/24 |
| 2004/0028561 A1 | 2/2004 | Daugherty et al. | 422/99 |

FOREIGN PATENT DOCUMENTS

| | | |
|---|---|---|
| DE | 2260729 | 5/1974 |
| EP | 0543108 A1 | 5/1993 |
| FR | 626191 | 8/1927 |
| JP | 59196713 | 11/1984 |
| WO | WO 98/58725 | 12/1998 |

OTHER PUBLICATIONS

Cassarly, William. "*Taming Light.*" "*Non-imaging optical systems focus on transferring light efficiently and controlling its distribution.*" Oe magazine, 7pp. <http://www.oemagazine.com/fromTheMagazine/dec02/taminglight.html>.

Cousins, Daniel. "*Biodefense of Passenger Aircraft.*" Biodefense Systems Group, MIT Lincoln Labroratory. Presented at FAA Center of Excellence. 23pp.

de la Mora, J.F. "Aerodynamic Focusing of Particles and Heavy Molecules, First Annual Report." *NTIS*. Feb. 16, 1988, 16 pages.

de la Mora, J.F. "Aerodynamic Focusing of Particles and Heavy Molecules. Final Report." *NTIS*. Jan. 8, 1990, 12 pages.

de la Mora, J.F. "Drastic Improvement of the Resolution of Aerosol Size Spectrometers via Aerodynamic Focusing: The Case of Variable-Pressure Impactors," *Chemical Engineering Communications*. vol. 151,1996, pp. 101-124.

de la Mora, J.F., et al. "Aerodynamic Focusing of Particles in a Carrier Gas." *Journal of Fluid Mechanic*. vol. 195, Oct. 1988, pp. 1-21.

Fernandez-Feria, R., et al. "Brownian-Motion Limited Aerodynamic Focusing of Heavy Molecules," *Rarefied Gas Dynamics*. Beylich, A.E., Ed., Proceedings of the 17th International Symposium on Rarefied Gas Dynamics, Jul. 8-14, 1990, pp. 214-221.

Foot, Virginia, E., et al. "*Characterising single airborne particles by fluorescence emission and spatial analysis of elastic scattered light.*" Defence Science and Technology Lab. (United Kingdom) 2pp, 2005 Copyright SPIE-The international Society for Optical Engineering. <http://spiedl.aip.or/GetabsServlet?prog=normal&id=PSISDG00561700000....>.

Frye-Mason, Greg et al. "*Novel fluorescence-based integrated sensor for chemical and biological agent detection.*" Nomadics, Inc. (USA) 2pp, 2005 Copyright SPIE-The international Society for Optical Engineering. <http://spiedl.aip.or/GetabsServlet?prog=normal&id=PSISDG00561700000....>.

Fuerstenau, S., et al. "Visualization of Aerodynamically Focused Subsonic Aerosol Jets." *Journal of Aerosol Science*. vol. 25, No. 1, Jan. 1994, pp. 165-173.

Hochrainer, D., Institut fur Aerobiologie. "Measurement of Aerosol Particle Size Distribution with an Improved Spectral Impactor." *NTIS* No. N7323533, 1973, 26pp.

Huston, Alan, L., et al. "*Optical classification of bioaerosols using UV fluorescence and IR absorption spectroscopy.*" Naval Research Lab. (USA) 2pp, 2005 Copyright SPIE-The international Society for Optical Engineering. <http://spiedl.aip.or/GetabsServlet?prog=normal&id=PSISDG00561700000....>.

Jeys, T.H., L., et al. "*Development of UV LED based biosensor.*" SPIE vol. 5071, 2003 Copyright SPIE., pp. 234-240.

Jurcik, B., et al. "On the Shape of Impactor Efficiency Curves," *Journal of Aerosol Science*. vol. 26, No. 7, 1995, pp. 1139-1147.

Kaye, Paul H., et al. "*A low-cost multi-channel aerosol fluorescence sensor for networked deployment.*" University of Hertfordshire (UK) and Defence Science Technology Lab (UK) 11pp, 2005 Copyright SPIE-The international Society for Optical Engineering. <http://spiedl.aip.or/GetabsServlet?prog=normal&id=PSISDG00561700000....>.

Liu, P., et al. "Optimizing the Detection Efficiency of a Low Pressure, In-Situ Particle Monitor Using Aerodynamic Focusing Lenses." *Proceedings—Institute of Environmental Sciences*. 1996, pp. 217-224.

Patent Cooperation Treaty Search Report, PCT-US98-12471, Corona Catalysis Corporation et al., Oct. 14, 1998.

Vance, Richard F., "Slanted Baffle Mist Eliminator". *US. Statutory Invention*. Registration No. H1499, Nov. 7, 1995.

\* cited by examiner

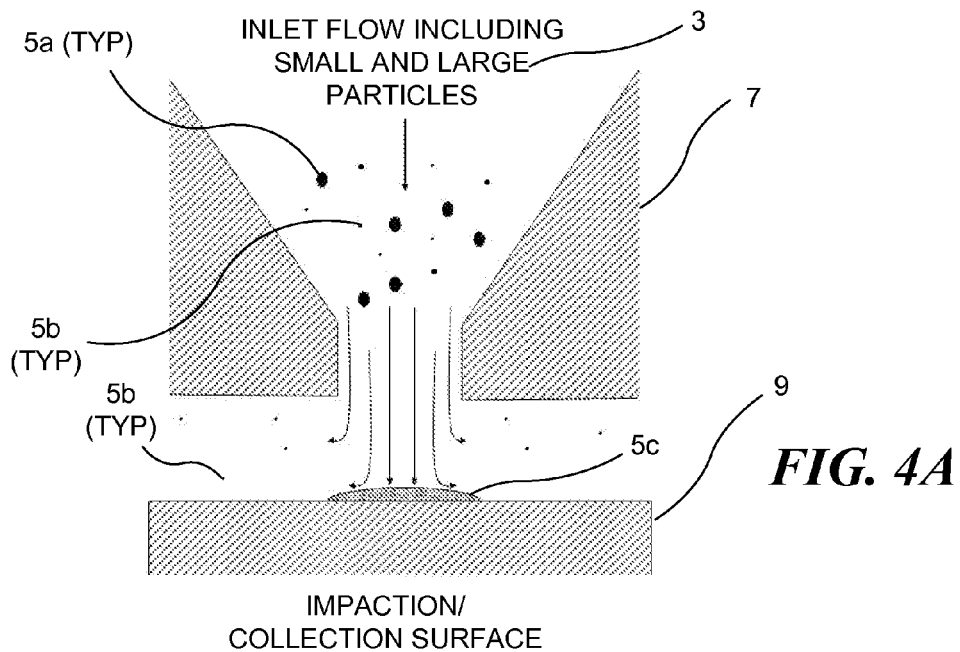
*FIG. 4A*
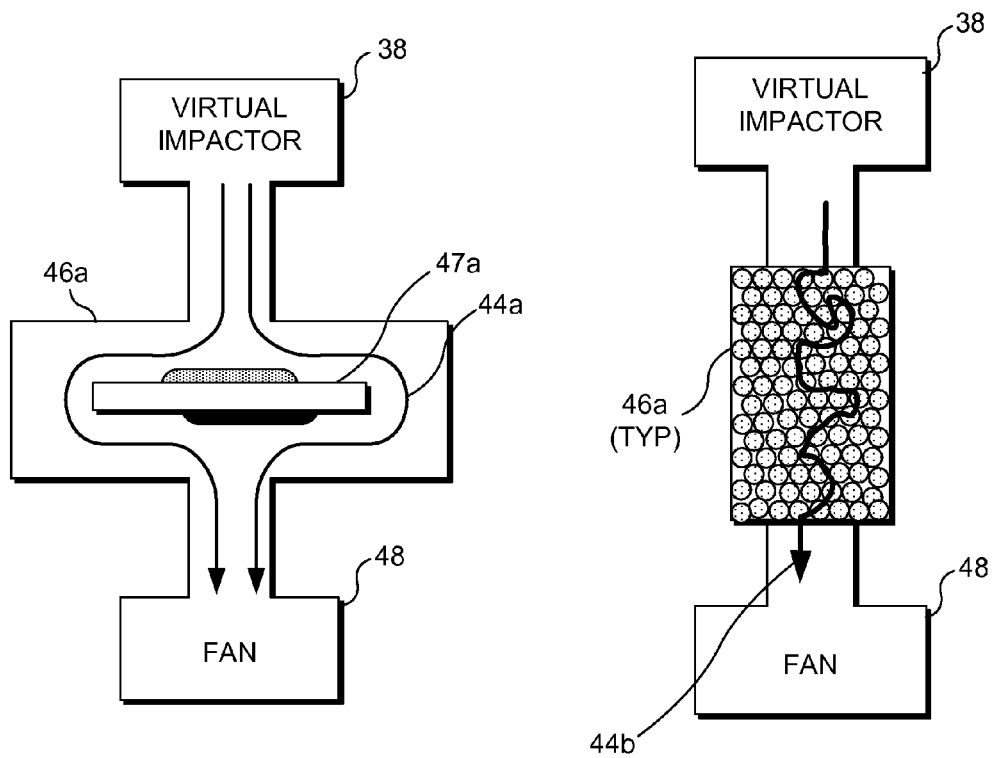
*FIG. 4B*  *FIG. 4C*

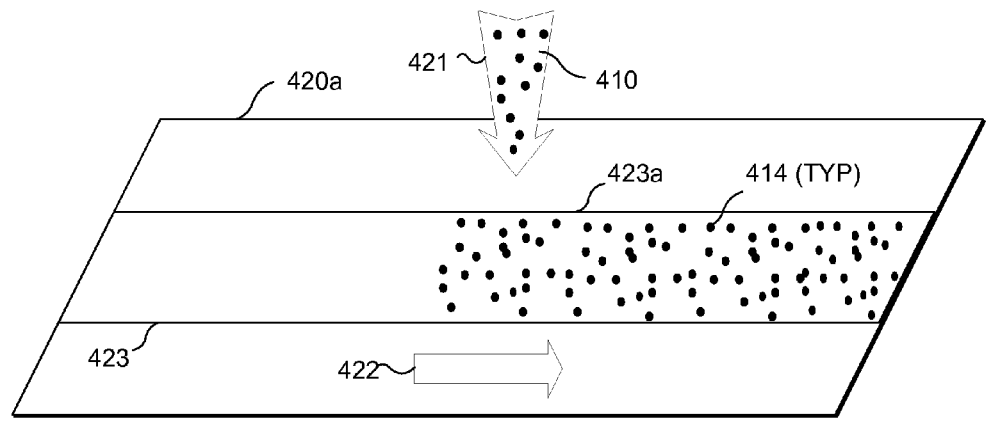
*FIG. 6C*
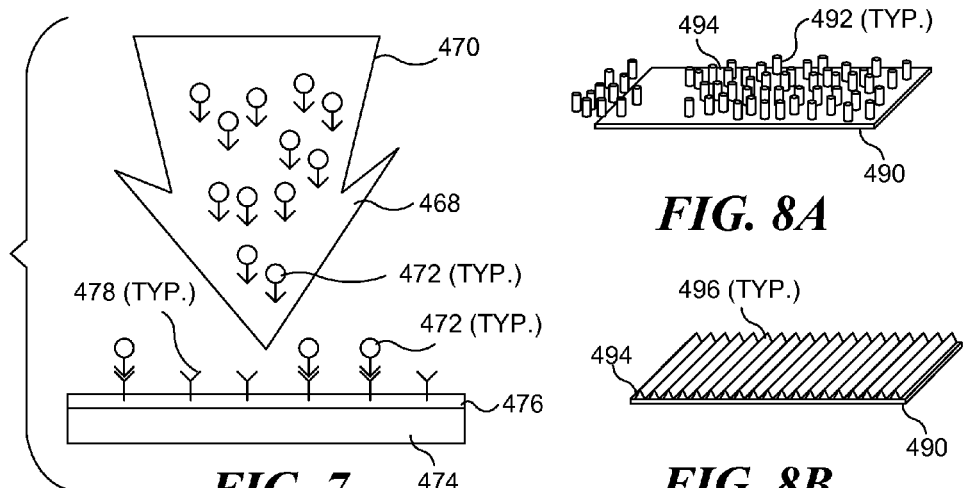
*FIG. 7*  *FIG. 8A*  *FIG. 8B*
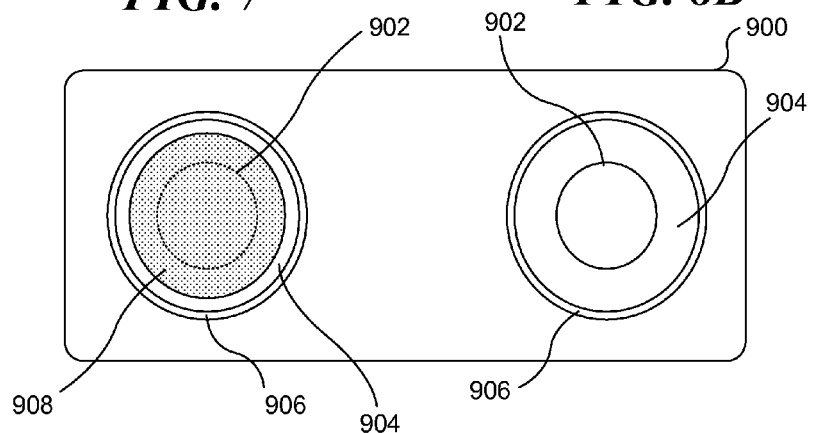
*FIG. 9A*

AIR SAMPLER BASED ON VIRTUAL IMPACTION AND ACTUAL IMPACTION

RELATED APPLICATIONS

This application is based on a prior copending provisional application Ser. No. 60/700,228, filed on Jul. 18, 2005, the benefit of the filing date of which is hereby claimed under 35 U.S.C. §119(e). This application is further a continuation-in-part of prior copending U.S. patent application Ser. No. 11/385,326, filed on Mar. 21, 2006, which is a continuation-in-part of prior U.S. patent application Ser. No. 11/058,442, filed on Feb. 15, 2005, which itself is a continuation-in-part of prior U.S. patent application Ser. No. 10/366,595, filed on Feb. 11, 2003, which issued as U.S. Pat. No. 6,938,777 on Sep. 6, 2005, which itself is based on a prior provisional patent application Ser. No. 60/355,915, filed on Feb. 11, 2002, the benefit of the filing dates of which is hereby claimed under 35 U.S.C. §119(e) and 35 U.S.C. §120. U.S. patent application Ser. No. 10/366,595 is further a continuation-in-part of a prior patent application Ser. No. 09/955,481, filed on Sep. 17, 2001, now issued as U.S. Pat. No. 6,695,146, the benefit of the filing date of which is also hereby claimed under 35 U.S.C. §120. Still further, copending patent application Ser. No. 11/058,442 is also a continuation of prior conventional application Ser. No. 10/066,404, filed on Feb. 1, 2002, which issued as U.S. Pat. No. 6,887,710 on May 3, 2005, and which is based on a prior provisional application Ser. No. 60/337,674, filed on Nov. 13, 2001, the benefit of the filing dates of which is hereby claimed under 35 U.S.C. §119(e) and 35 U.S.C. §120. Conventional application Ser. No. 10/066,404 is also a continuation of a prior conventional application Ser. No. 09/775,872, filed on Feb. 1, 2001, which issued as U.S. Pat. No. 6,729,196 on May 4, 2004, and which is a continuation of a prior conventional application Ser. No. 09/265,619, filed on Mar. 10, 1999, which issued as U.S. Pat. No. 6,267,016 on Jul. 31, 2001, and Ser. No. 09/265,620, filed on Mar. 10, 1999, which issued as U.S. Pat. No. 6,363,800 on Apr. 2, 2002, the benefit of the filing dates of which is hereby claimed under 35 U.S.C. §120.

BACKGROUND

The separation and collection of particulates/aerosols from an air stream (or other fluid stream) is of concern in several contexts. In some cases, the goal may be to simply remove the particulates/aerosols from the fluid stream, thereby cleaning or purifying the fluid. Often it is desired to remove all particulates, regardless of composition, if the particulates are above a certain size. For example, automobile painting and the fabrication of silicon chips in clean rooms represent two situations in which all particulates large enough to result in an inferior product are desirably removed from the processing environment.

In other cases, particulates are collected for analysis to determine the type and concentration of such particulates/aerosols entrained in the fluid. For example, this technology may be employed in the detection of airborne biological or chemical warfare agents, the detection of biological contamination in confined spaces, such as aircraft or hospitals, or the detection of industrial pollutants (either in ambient fluid or in the effluent of smokestacks).

Much effort has been expended in the past in the detection and classification of particulates or aerosols in fluid streams. Various technologies have been employed to remove particles from an air stream to obtain a sample for analysis, including cyclones, impactors, and filters. Impactors generally direct a stream of fluid containing the particulates toward an impactor plate. Due to their inertia, the particulates striking the impactor plate are collected on its surface, while the fluid is deflected to the side. One potential problem with such impactors is that particulates may bounce off the impactor's collection surface upon impact and thus avoid collection. It would be desirable to provide improved impactors that minimize such an undesirable characteristic.

Virtual impactors have been used to sort particulates entrained in a flow of fluid based on particle size, as well as to increase the concentration of particles of a desired size. When used in connection with an impactor, greater control over the particles deposited on the impaction surface can be achieved. Virtual impactors may operate on a number of different principles, but all avoid actual "impact" as a means to separate particulates from a fluid in which the particulates are entrained, and rely on differences in particulate mass to induce inertial separation. Specifically, a particulate-laden fluid stream is directed toward a surface presenting an obstruction to the forward movement of the fluid stream. The surface preferably includes a void at the point where the particulates would normally impact the surface, to minimize actual impaction. When a major portion of the fluid stream changes direction to avoid the obstruction presented by the surface, fine particulates remain entrained in the deflected major portion of the fluid stream. Heavier or denser particulates, on the other hand, fail to change direction and remain in a minor portion of the fluid. The threshold particulate size that generally determines whether a particle will be entrained in the minor flow or the major flow is referred to as the cut size. For example, a virtual impactor having a cut size of 10µ will separate a flow of fluid into a major flow containing the majority of the fluid and the majority of particles smaller in size than 10µ, and a minor flow that includes a minor portion of the fluid, and a majority of the particles over 10µ. The concentration of particles over 10µ in the minor flow is thus substantially increased (due to the reduction in volume of the fluid in the minor flow). Concentration increases of about 10-fold are readily achievable, and virtual impactors in series can readily achieve concentration increases of about 100-fold. Some examples of virtual impactors can be found in U.S. Pat. Nos. 3,901,798; 4,670,135; 4,767,524; 5,425,802; and 5,533,406.

Once particulates have been collected (for example, deposited on an impaction surface), the particles can be analyzed to characterize the particles (i.e., biological or not, for example, using relatively simple optical techniques) or to more specifically identify the particles (which may require application of more sophisticated analytical techniques). The specific analytical technique employed will dictate whether the particles on the collection surface can be analyzed in place, or whether a liquid or gaseous sample needs to be obtained before analysis.

Accordingly, a need exists to develop a method and apparatus capable of providing samples collected from a fluid stream with minimal operator effort, and minimal chance of contamination. Such samples desirably should include a high concentration of particulates of a desired size. It would further be desirable to provide method and apparatus for removing collected particulates from an impact collection surface, and to transfer such particulates in a liquid or gaseous state to an appropriate analytical component for analysis. To facilitate adoption of such technology, it would be desirable for such apparatus to exhibit minimal operational costs and require minimal operator involvement once the apparatus has been properly configured.

SUMMARY

Overview of the Concepts Presented Herein: The concepts disclosed herein are directed to a number of exemplary methods and apparatus for removing particles/particulates from a fluid stream and depositing such particles/particulates on one or more collection surfaces. Preferably, a concentrator is employed to increase a concentration of particles larger than a first predefined particle size in at least a portion of the fluid, thereby achieving a concentrated volume of fluid. While it should be recognized that the concepts disclosed herein can be applied to removing particles from many different kinds of fluids, a particularly useful application is removing particles from air. However, where the following description specifically uses the term "air," it should be recognized that the concepts being discussed can also be applied to other fluids. Thus, the concepts being disclosed are generally not intended to be limited to removing and/or collecting particles and particulates from air alone. The concentrated volume of fluid is then directed to the collection surface(s), such that particles in the concentrated volume of fluid are deposited upon the collection surface(s). Preferably, the concentrator is implemented using a virtual impactor. Such a virtual impactor generates a minor flow including a minor portion of the concentrated volume of air and a major portion of particles larger in size than the first predefined particle size, and a major flow including a major portion of the concentrated volume of air and a minor portion of particles larger in size than the first predefined particle size. The minor flow is directed to the collection surface(s) for removal of the particles.

In some exemplary embodiments, the collection surface comprises a plurality of beads, where the beads are substantially larger than the particles in the fluid stream. The fluid stream containing the particles is passed through a bed of beads. The particles are removed from the fluid stream as the particles impact various beads as the fluid stream traverses the bed of beads. Significantly, the bead bed substantially enhances collection efficiency, because if a particle just misses or bounces off one bead, it will likely encounter additional beads upon which it may impact and adhere. If a single impaction surface is employed, it is possible that particles bouncing off the single impaction surface will not be collected.

In some exemplary embodiments, a pre-filter is used to remove particles larger than a second predefined particle size. For example, a pre-filter removing particles larger than about 10μ can be employed (because many particles of interest may be smaller than 10μ in size). The pre-filter can be implemented using a filter comprising a plurality of pores smaller in size than the second predetermined particle size, an impactor, or a virtual impactor. When a virtual impactor is employed, the major flow, comprising the majority of the volume of fluid and a majority of particles smaller in size than the second predefined particle size is conveyed to the concentrator.

In some exemplary embodiments, a sample preparation component is configured to generate at least one of a gaseous sample and a liquid sample including particles removed from the concentrated volume by the collection surface(s). In some cases, the sample is generated without requiring removal of the collection surface(s) from the apparatus. To generate a gaseous sample, a heater or laser can be used to vaporize particles deposited upon the collection surface. To generate a liquid sample, a rinse liquid can be used to wash particles from the collection surface. In some exemplary embodiments, an analytical component is included to analyze the sample generated by the sample preparation component. In some embodiments, the sample is thus analyzed without requiring removal of the sample from the apparatus.

In some exemplary embodiments, the collection surface includes a coating configured to enhance collection of particles from the concentrated fluid stream. The coating can comprise a material characterized by its ability to retain particles impacted thereon when dry, and having a relatively low coefficient of adhesion when wet, so that the particles that have impacted on the collection surface and been retained thereon are readily washed from the surface with a liquid. The coating can comprise a material that attracts substantially only biological particles of a specified type, for efficiently separating said particles from the concentrated volume of fluid, the coating binding with the particles of the specified type to retain them on the collection surface. The coating can comprise a material that changes state while being retained on the collection surface, a first state of the material characterized by its ability to retain the particles that impacted thereon, separating the particles from the concentrated volume of fluid, and a second state of the material being characterized by its ability to readily release the particles separated from the concentrated volume of fluid.

It should be recognized that other aspects of this technology also encompass exemplary methods incorporating steps substantially similar to the functions implemented by the elements discussed above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A is a block diagram schematically illustrating the basic functional elements of an exemplary air sampler implementing the concepts disclosed herein;

FIG. 1B schematically illustrates a portable air sampler implementing the elements of FIG. 1A;

FIG. 2 is a block diagram schematically illustrating functional elements of another exemplary air sampler implementing the concepts disclosed herein;

FIG. 3A schematically illustrates an exemplary filter comprising a plurality of pores that can be used to implement the pre-filter of FIG. 1A;

FIG. 3B schematically illustrates an impactor including an impaction plate that can be used to implement the pre-filter of FIG. 1A;

FIG. 3C schematically illustrates a virtual impactor that can be used to implement the pre-filter of FIG. 1A;

FIG. 4A schematically illustrates an exemplary virtual impactor and impaction plate being used to deposit a plurality of particles on the impaction plate;

FIG. 4B schematically illustrates an exemplary configuration between a virtual impactor, an impaction plate configured to act as a collection surface, and a fan that can be implemented in the air samplers disclosed herein;

FIG. 4C schematically illustrates an exemplary configuration between a virtual impactor, a plurality of beads configured to act as a collection surface, and a fan that can be implemented in the air samplers disclosed herein;

FIG. 4D schematically illustrates an exemplary configuration between a virtual impactor, a porous substrate configured to act as a collection surface, and a vacuum that can be implemented in the air samplers disclosed herein;

FIG. 6C is a schematic view of a flexible tape having a continuously coated impact collection surface;

Figure 9B:
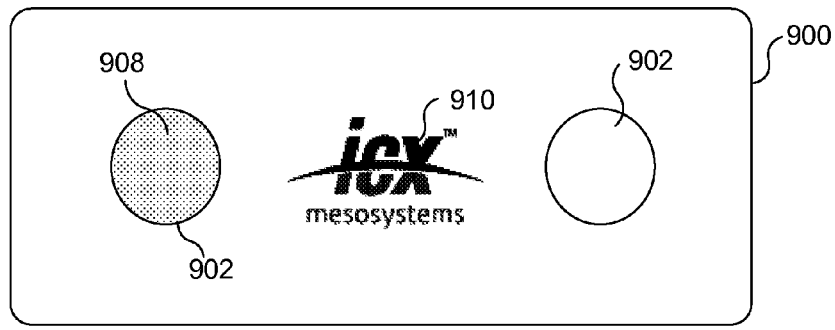
Figure 9C:
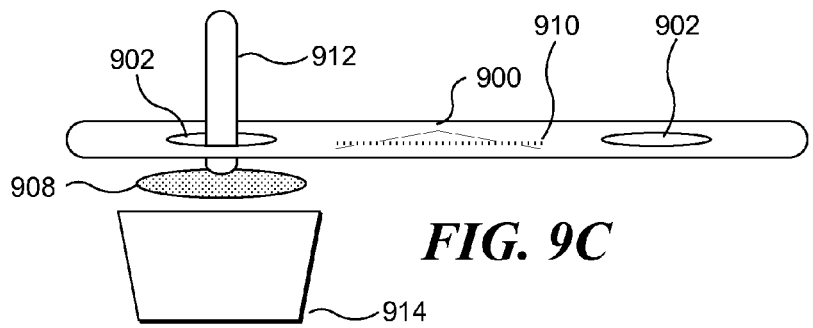
Figure 9D:
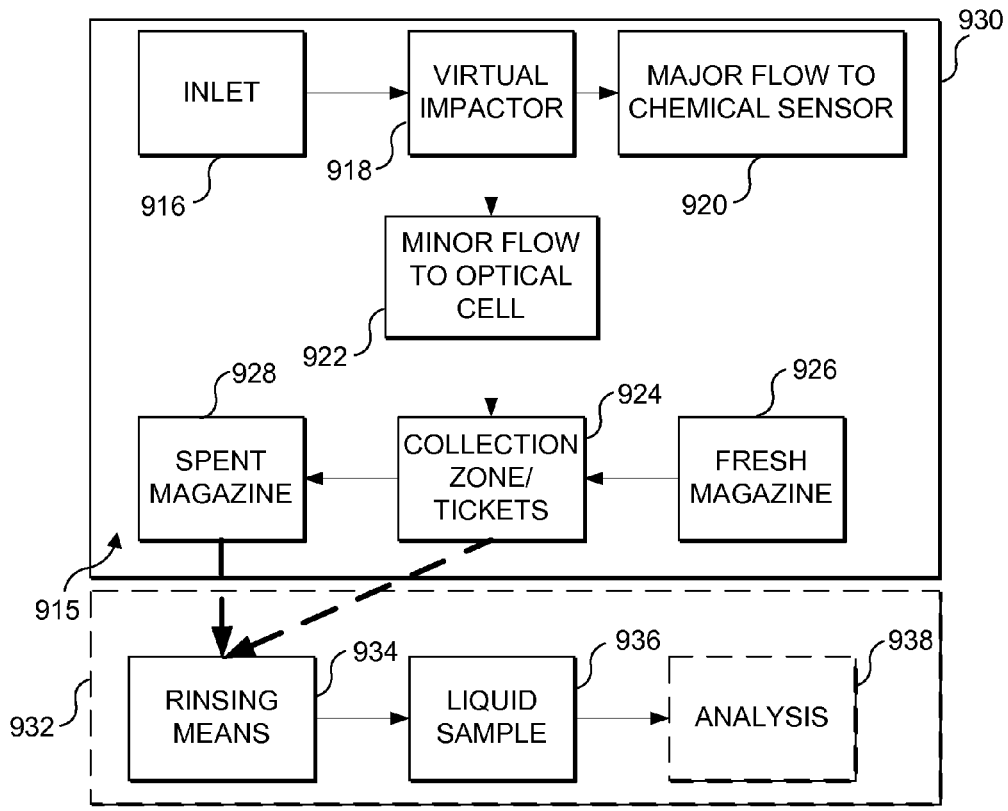
Figure 9E:
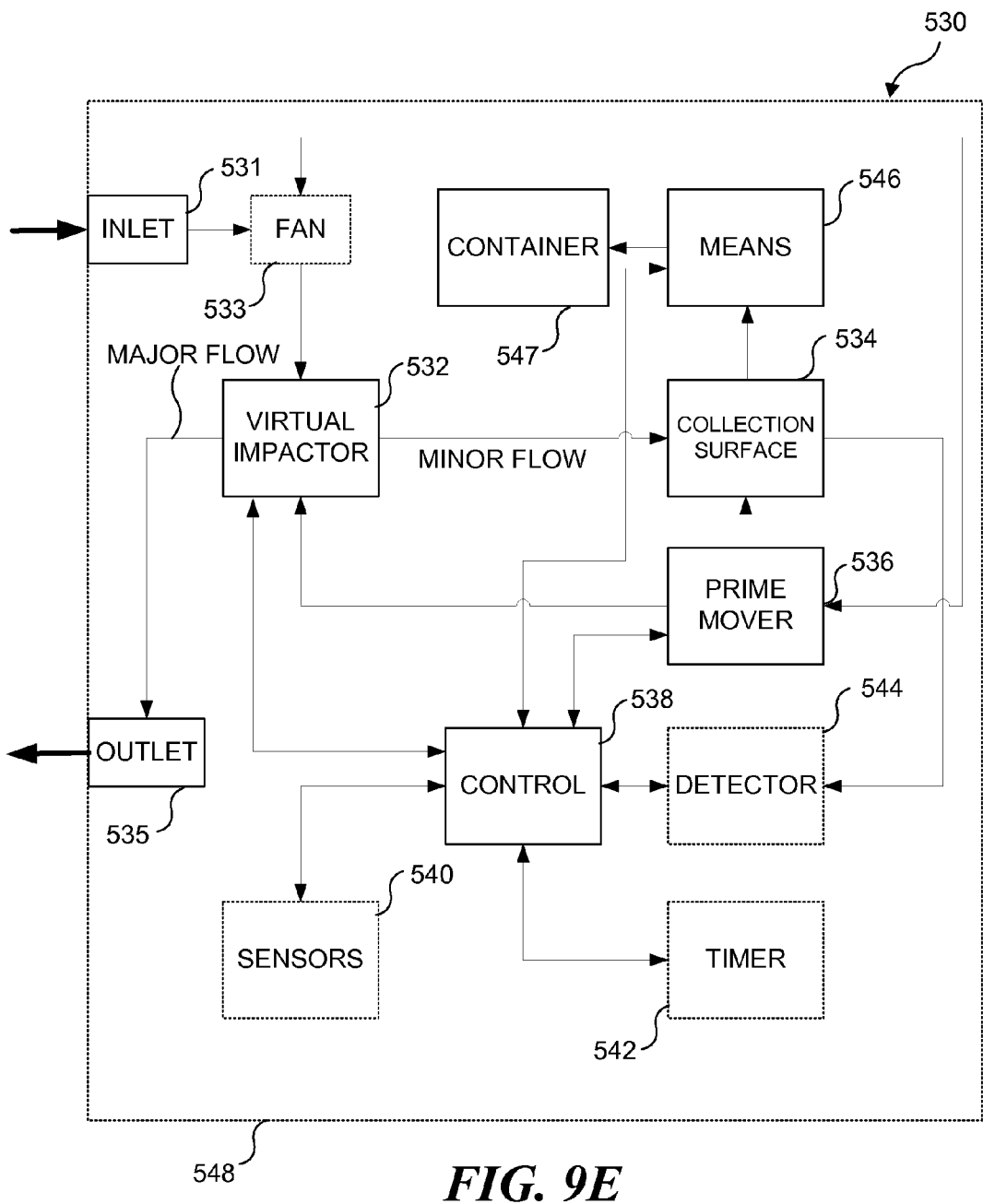
Figure 10:
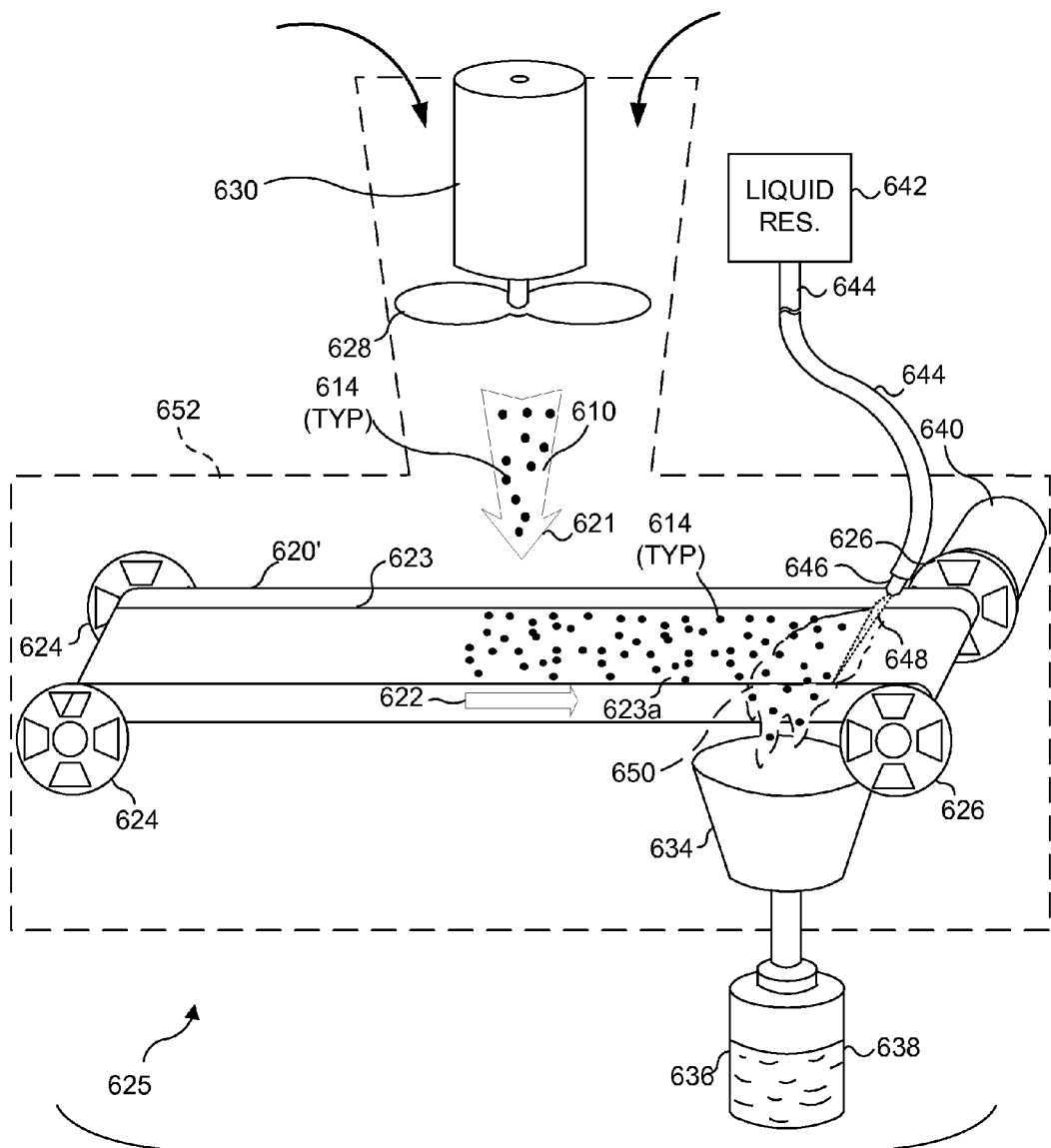
Figure 11A:
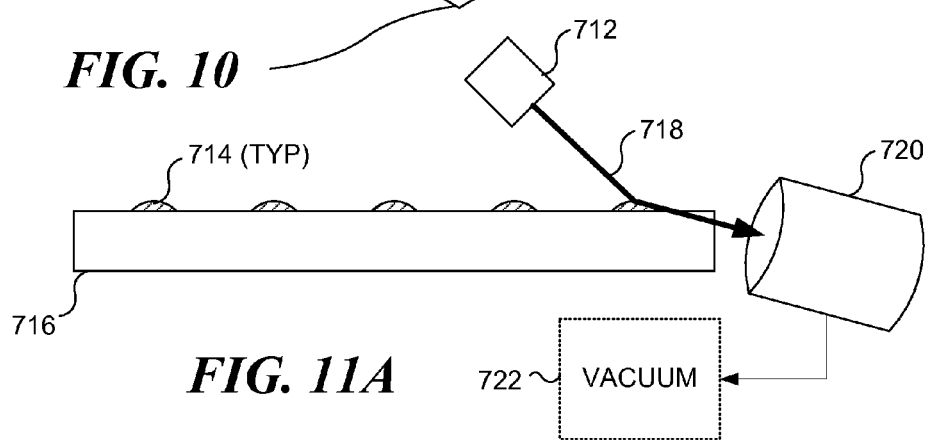
Figure 11B:
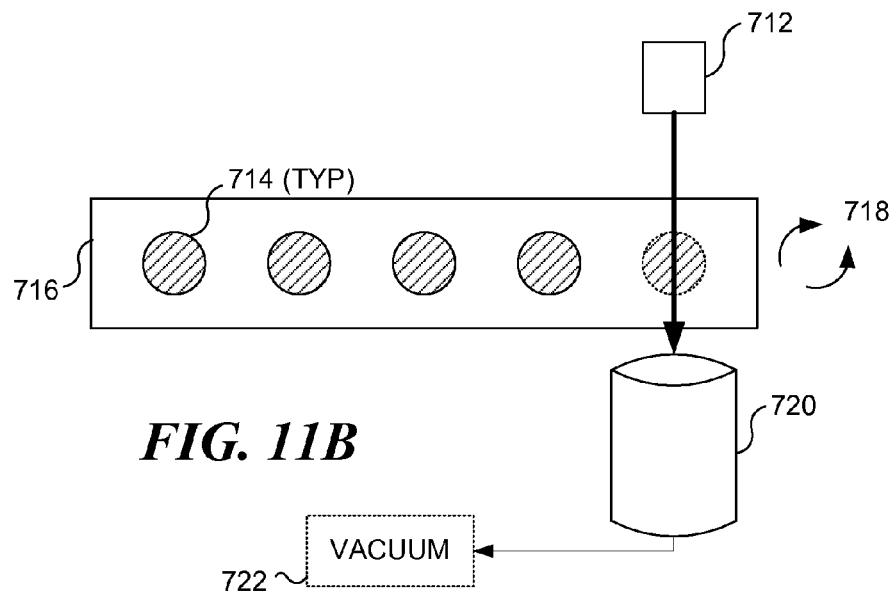
Figure 12A:
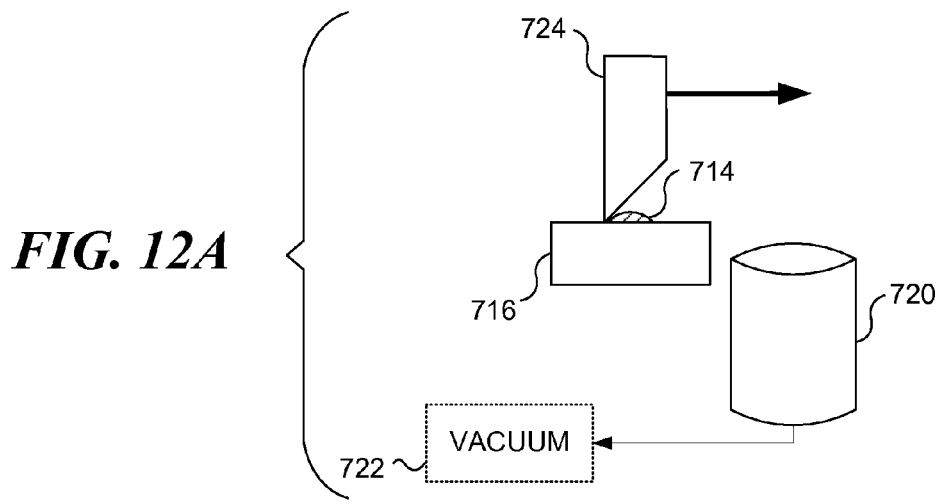
Figure 12B:
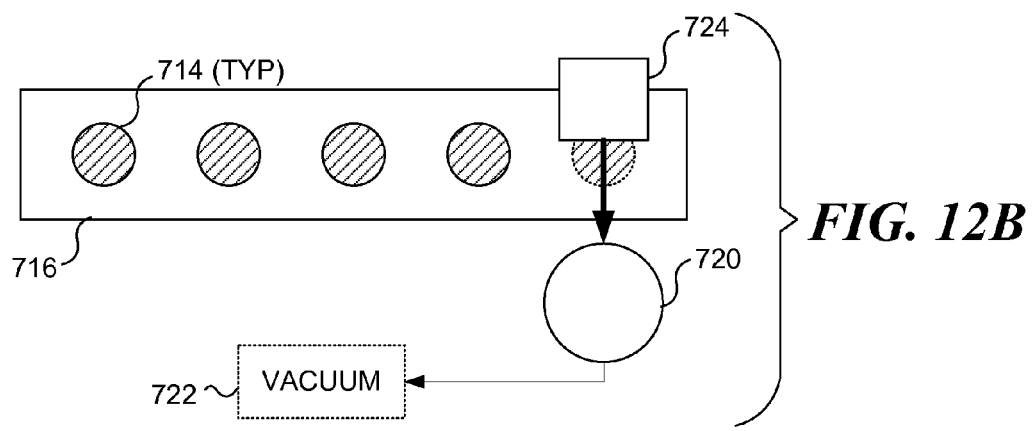
Figure 13:
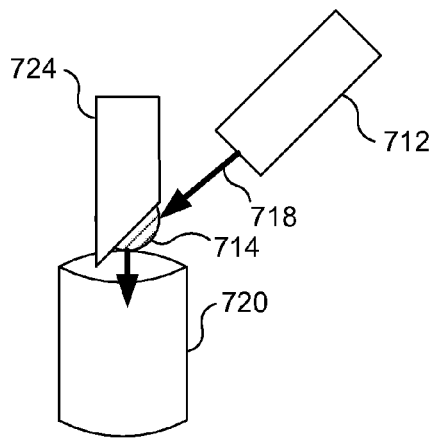
Figure 14:
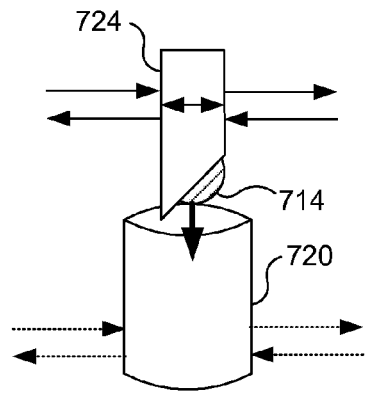
Figure 15A:
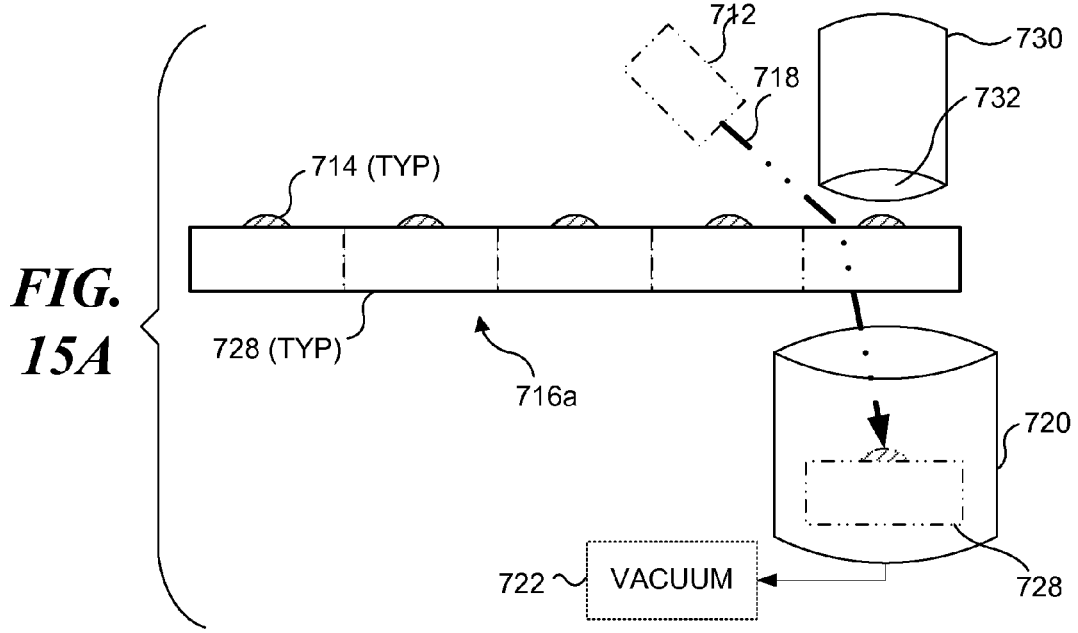
Figure 15B:
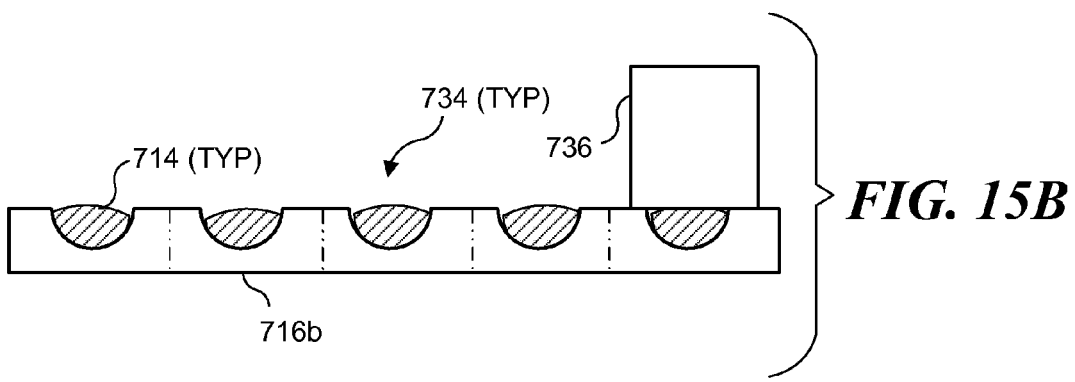
Figure 16:
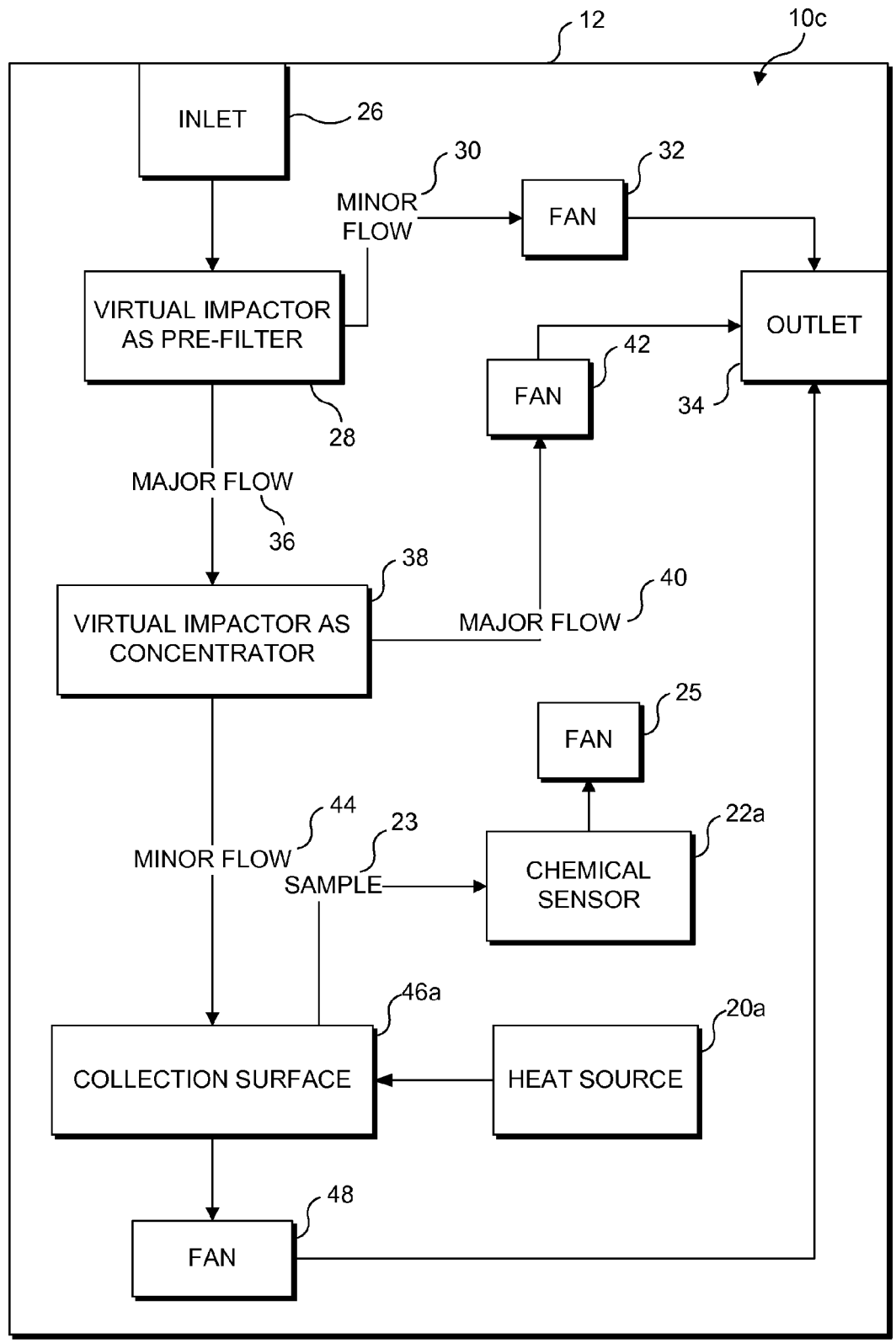
Figure 17:
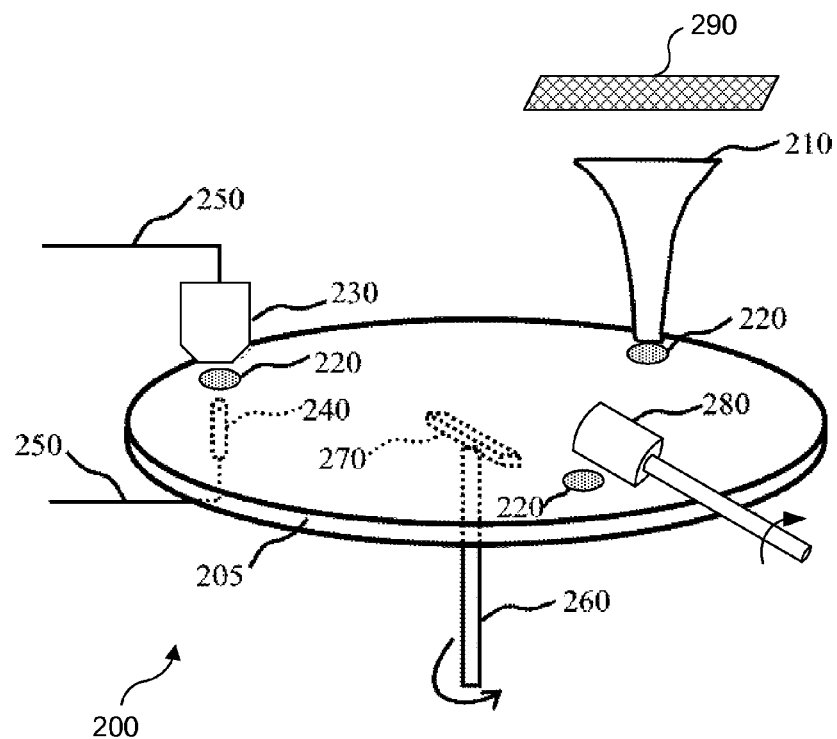
Figure 18:
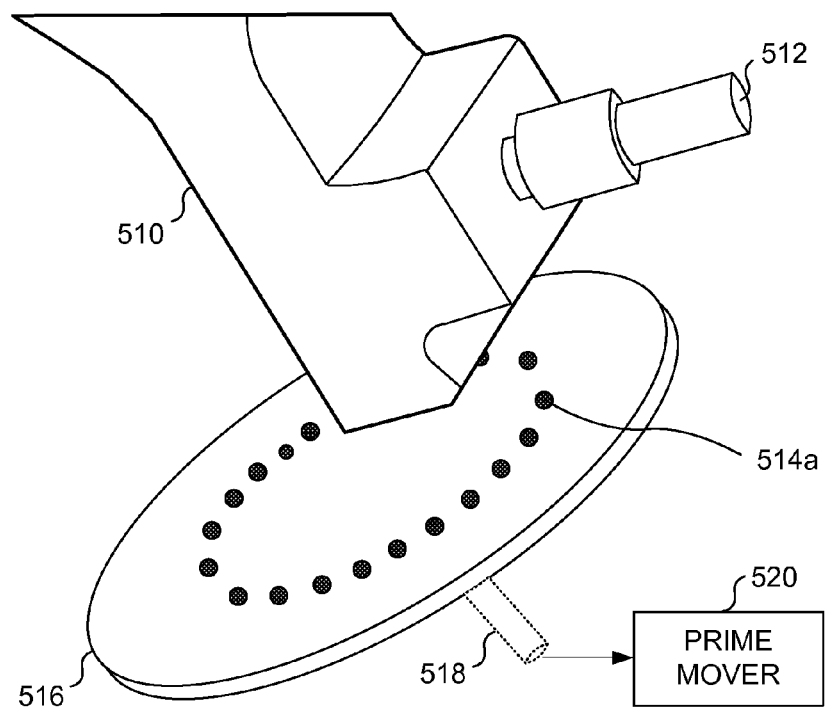

FIG. 7 schematically illustrates an impact collection surface coated with a material that includes antibodies selected to link with an antigen on a specific biological particulate;

FIGS. 8A and 8B schematically illustrate two exemplary embodiments in which outwardly projecting structures are provided on an impact collection surface to enhance particulate collection;

FIG. 9A is a plan view of an exemplary ticket including two collection areas for use in an exemplary particle collection system;

FIG. 9B is a bottom view of the ticket of FIG. 9A;

FIG. 9C is a side view of the ticket of FIGS. 9A-B, illustrating a punch being used to remove a disposable collection surface;

FIG. 9D is a block diagram of the components of an exemplary particle collection system utilizing the ticket of FIGS. 9A-C;

FIG. 9E is a block diagram of the components of an exemplary particle collection system;

FIG. 10 is a schematic view of an integrated system using a liquid rinse to collect a sample of particles from a collection surface;

FIG. 11A is a block diagram of an embodiment in which a fluid jet is used to collect a sample of particles from a collection surface in accord with one aspect of the concepts disclosed herein;

FIG. 11B is a block diagram of an embodiment in which the collection surface can be rotated 90 degrees to enable a fluid jet to be used to collect a sample of particles;

FIG. 12A is a side view of an embodiment in which a mechanical blade is used to collect a sample of particles from a collection surface in accord with one aspect of the concepts disclosed herein;

FIG. 12B is a plan view of an embodiment in which a mechanical blade is used to collect a sample of particles from a collection surface in accord with one aspect of the concepts disclosed herein;

FIG. 13 is a block diagram illustrating an embodiment in which a mechanical blade is rinsed to remove particles from the blade;

FIG. 14 is a block diagram of an embodiment in which a mechanical blade is vibrated to remove particles from the blade;

FIG. 15A is a block diagram of an embodiment in which a portion of a collection surface on which particles have been collected is removed and placed into a sample container;

FIG. 15B is a block diagram of an embodiment in which a portion of a collection surface that includes surface features into which particles have been collected is removed and placed into a sample container;

FIG. 16 is a block diagram of an embodiment in which a heat source such as a laser or heater is used to heat a portion of a collection surface to vaporize particles deposited thereon, to generate a gaseous sample that is drawn into a chemical sensor;

FIG. 17 schematically illustrates an exemplary particle detection system including means to regenerate a collection surface for continued operation; and FIG. 18 is an isometric view of a virtual impactor and a deposition/collection substrate.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

In the following description, the prefix "micro" is applied generally to components that have sub-millimeter-sized features. Micro-components are fabricated using micro-machining techniques known in the art, such as micro-milling, photolithography, deep ultraviolet (or x-ray) lithography, electro-deposition, electro-discharge machining (EDM), laser ablation, and reactive or non-reactive ion etching. It should be noted that micro-machined virtual impactors provide for increased collection efficiency and reduced pressure drops.

Also as used hereinafter, the following terms shall have the definitions set forth below:

Particulate & particle—any separately identifiable solid, semi-solid, liquid, aerosol, or other component entrained in a fluid stream that has a greater mass than the fluid forming the fluid stream, and which is subject to separation from the fluid stream and collection for analysis. It is contemplated that the particulates & particles may arise from sampling almost any source, including but not limited to, air, water, soil, and surfaces, and may include inorganic or organic chemicals, or living materials, e.g., bacteria, cells, or spores.

Fluid—any fluid susceptible to fluid flow, which may comprise liquids or gases, and which may entrain foreign particulates & particles in a flow thereof. Unless otherwise noted, "fluid" shall refer to an ambient or source fluid containing un-concentrated particulates that are subject to collection, not a fluid into which the particulates are concentrated after collection or capture.

Spot—an aggregate of particulates or particles deposited upon a collection surface in a relatively small area, so that the individually small particulates are aggregated together to form a collection of such particles larger than a single such particle, which can be more readily observed by magnification or by the naked eye.

The following description first describes an embodiment for an exemplary particle sampler in terms of its basic functional elements. Then, each functional element is discussed in greater detail, and finally, additional exemplary embodiments are discussed.

Figure 1A:
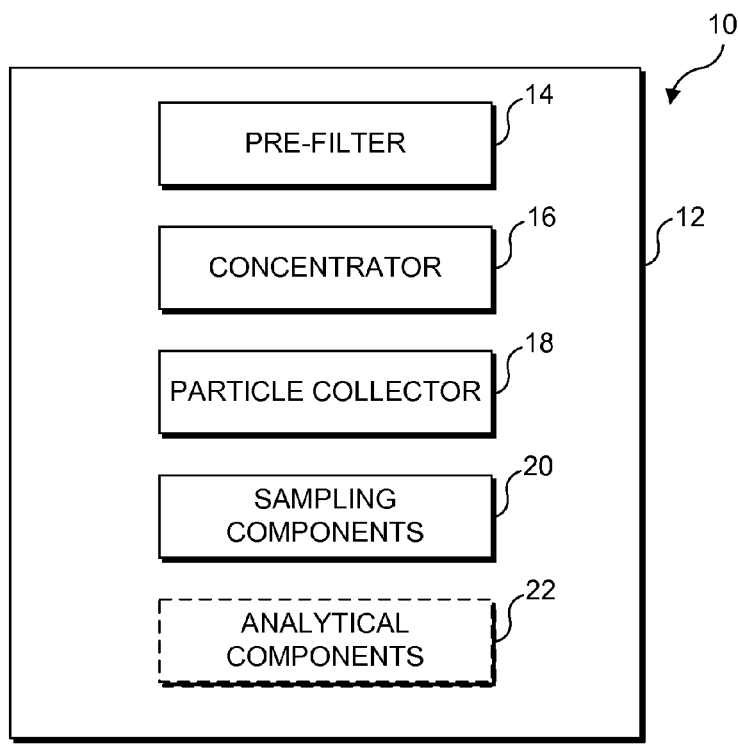

FIG. 1A is a functional block diagram schematically illustrating the basic functional elements of an embodiment for an exemplary air sampler 10, which includes a housing 12, a pre-filter 14 (which in some embodiment may partially extend beyond the housing), a concentrator 16, a particle collector 18, a sampling component 20, and an analytical component 22 (note that the block corresponding to the analytical component is shown using dash lines to indicate that the analytical components are optional elements; however, in some embodiments, one or more analytical components are included). Commercial embodiments of sampler 10 are likely to be available with and without the analytical component(s), such that customers already having analytical components (such as chemical sensors, biological sensors, or other analytical instruments) can use the air sampler with the equipment that they already have. While sampler 10 is discussed in the terms of an air sampler, since air samplers represent particularly useful implementations of the concepts disclosed herein, it should be recognized that particles can be entrained in flows of other types of fluid, and the concepts disclosed herein are not intended to be limited only for separating particles from air.

Housing 12, while not strictly required, is preferably implemented to protect the additional functional elements discussed below, and to facilitate transportation of the air sampler. Those of ordinary skill in the art will readily recognize that air samplers of many different form factors and sizes can be implemented consistent with sampler 10. Relatively larger air samplers capable of sampling relatively larger volumes (or volumetric flows) of air may be implemented in buildings, whereas relatively smaller air samplers can be made to be portable, so as to be readily moved from one location to the next to sample air (or other fluid) in a plurality of different locations.

Pre-filter 14 is a device that performs one or more of the following functions: (a) removes over-sized particles that are too large to be of interest (for example, those greater than 10 microns in diameter), (b) rejects or removes rain, snow, and other water precipitation, (c) restricts insects from crawling or flying into the apparatus, and (d) rejects or removes other flying debris. Rejecting oversized particles may be a desired functionality for some applications. As discussed in greater detail below, pre-filters can be implemented using inertial impactors configured to remove such oversized particles (the term oversize indicating that the particles are larger than a particle size that is of particular interest), virtual impactors, or filters including a plurality of pores smaller in size than the oversized particles.

Concentrator 16 is configured to discard a portion of the air introduced into the concentrator without also discarding a majority of the particles of interest, thereby increasing the concentration of particles of interest in the remaining portion of the air (i.e., that portion of the air that has not been discarded) to enhance collection efficiency. Virtual impactors represent a particularly preferred technology used to implement such concentrators. A virtual impactor is a device that will separate a fluid flow (such as air) into a minor flow (i.e., a smaller fraction of the fluid flow) containing a majority of particles larger than a cut size, and a major flow (i.e., a major fraction of the fluid flow) containing particles smaller than the cut size. Virtual impactors are available that exhibit relatively low pressure drops (which may be desirable because relatively low pressure drops minimize power requirements) across each stage and that can be injection molded at a relatively low cost. When an impactor surface is introduced into the minor flow, a relatively high collection efficiency can be obtained. Depending upon a nozzle size associated with the outlet of the minor flow, a spot size of less than 3 mm can be generated on the collection surface. Such small size has the advantage of concentrating the collected particles in a relatively small area, which simplifies subsequent removal of such particles to obtain a sample. The virtual impactor provides initial particle concentration by separating particles of interest from the bulk of the fluid flow. For example, particles ranging from about 1 to about 10μ in size can be concentrated, and the volumetric flow of air significantly reduced. Multiple virtual impactors can be arranged in series to achieve higher particle concentrations.

Particle collector 18 is configured to collect particles of interest from the remaining portion of air (i.e., that portion of the air that has not been discarded by the concentrator). In general, particle collector 18 includes one or more collection services that remove particles from the air by impaction (i.e., the particles entrained in the air collide with the collection surface and are retained thereon). The concepts disclosed herein encompass several different types of collection surfaces. As discussed in greater detail below, collection surfaces can be treated with specialized coatings to enhance collection efficiency.

Sampling component 20 is configured to obtain a sample from the particles deposited upon the collection surface, and to prepare the particles for analysis by an analytical component. The type of sample obtained and the sample preparation required will vary depending on the specific analytical component employed. For example, some analytical components require dry samples, some require wet samples (i.e., samples contained in a volume of liquid), and still other types of analytical components require gaseous or vaporous samples. Gaseous and vaporous samples can be obtained by desorbing a sample from a surface using heat (which can be supplied by various elements, such as an infrared lamp, an electrical resistive heater, or a laser). Gaseous/vaporous samples can also be obtained by dissolving the sample in a solvent and flash vaporizing the solvent. Since the use of relatively large volumes of solvents/reagents in field samplers is undesirable, because providing the solvents/reagents presents an additional logistics problem, it may be desirable to employ an air sampler that uses minimal volumes of such solvents/reagents.

In at least some embodiments sampling component 20 can regenerate the collection surface in the process of obtaining the required sample. The term "regenerating the collection surface" should be understood to mean removing the collected/deposited particulates, such that previously collected particulates will not contaminate future samples. Such regeneration can be achieved in a plurality of different ways, some of which are discussed in detail below. Where a liquid sample is obtained, rinsing the collection surface may simultaneously obtain the sample and regenerate the collection surface. Where a vaporous sample is obtained, heating the particulates/collection surface may simultaneously obtain the sample and regenerate the collection surface. In other embodiments, relative motion between particle collector 18 (i.e., the collection surface) and the minor flow outlet of concentrator 16 enables particles to be deposited on different portions of the collection surface over time, such that previously deposited particles do not contaminate subsequent samples. In such an embodiment, regeneration of the collection surface is not required (although such functionality may be implemented if desired). The relative motion can be achieved by coupling a prime mover to at least one of the minor flow outlet (or the outlet of a conduit through which the minor flow is directed) and the collection surface.

In some embodiments, a portion of the collection surface may be removed to obtain a sample, and another portion of the collection surface is placed in fluid communication with the concentrator to collect additional particles to be used to obtain a future sample. In still other embodiments, a mechanism is included to clean the collection surface after a sample has been collected. Such cleaning mechanisms include, but are not limited to, liquids, compressed air, cleaning pads, and cleaning brushes.

As noted above, analytical component 22 can be implemented using various types of analytical instruments, including but not limited to: fluorescence-based sensors; chemical sensors; particle counters; spectrophotometers; gas chromatographs (GC); mass spectrographs (MS); and combinations thereof (for example, a GC/MS). Clearly, the sampling component implemented is based on the analytical component that will be employed.

Not specifically shown in FIG. 1A are additional components, such as tubing and hoses used to move air from one portion of the sampler to another, an inlet to introduce air into the air sampler, one or more exhaust ports to discard air, fans or pumps to move air through the air sampler, a battery or other electrical power source (or an electrical conductor configured to bring electrical power into the air sampler from an outside source, such as line voltage) to energize components requiring electrical power, a data port configured to enable analytical data to be output from the analytical component, and a controller configured to control overall operation of the air sampler. FIG. 1A is provided to highlight the most important functional elements of air sampler 10, and those of ordinary skill in the art will readily recognize that the elements noted above as not shown will likely be incorporated into the air sampler to enhance its functionality or utility. Additional Figures discussed in detail below (in particular, FIG. 2) provide additional information relative to some of these other components.

Several factors, beyond the type of analytical component that will be used to analyze the sample obtained by air sampler 10, can affect the specific implementation employed. For example, the flow rate of the sampler is dependent upon the power requirement and size requirement of the sampler. Thus, air samplers intended to have higher flow rates will generally be larger and require more power. For portable air samplers, small size and small power requirements (hence relatively low flow rates) are generally preferred; however, greater performance can be achieved using larger sizes and more power. Higher flow rates generally correspond to higher sensitivities. For portable units, battery-based power supplies will represent a significant percentage of the weight of the sampler.

In determining a design for a sampler, each of the following can represent an important consideration: environmental compatibility, sensor system compatibility, concentration factor, particle size selectivity, reliability, logistics (size, weight, power, and noise), operating cost, and initial cost. Different end-users having different applications in mind will weigh these factors accordingly, based on their requirements. Some trade-off between these parameters might be employed to customize a sampler design to the specific requirements of a user.

With respect to sensor system compatibility, a critical question to be answered is for what purpose will the sampler be used? Some exemplary uses include: initial warning or screening of air samples for bio or chemical hazards in the field; chemical identification of samples in the field; chemical confirmation of samples in the lab; and forensics investigations.

With respect to environmental compatibility, relevant factors associated with outdoor environments include operating humidity, temperature, susceptibility to wind, rain, and the presence of pollutants in the environment (such as engine exhaust and other pollutants in an urban environment). Relevant factors associated with indoor environments can include: low humidity (often associated with mail rooms), a high loading of paper dust (also often associated with mail rooms), and a high loading of other particulate contaminants (often associated with battlefields and subways).

Concentration factor is a measure of the effectiveness of the sampler to concentrate aerosols for a specific application. Low vapor pressure chemicals may be present in an aerosol form, or may be impregnated into or condensed onto a carrier aerosol.

Particle size range is another factor; respirable particles (i.e., particles that may be of particular interest because their relatively small size allows them to be inhaled) are generally considered to be particles ranging in size from about $1\mu$ to about $10\mu$. Chemicals in the air may be in the form of submicron particulates or vapors. Low vapor pressure chemicals may pose a threat over a much broader range (e.g., from about $0.01\mu$-$100\mu$). The size of the particles of interest (i.e., those particles the air sampler is specifically configured to collect) will affect the design of the pre-filter, the concentrator, and the particle collector, because such elements can be specifically configured to enhance collection of particles of a predefined size (or size range).

In one exemplary embodiment, preferred (but not limiting) design parameters for sampler 10, which is intended to output a liquid sample, include continuous autonomous operation, relatively high flow rate (up to 800 L per minute, with a particularly preferred range being about 300-400 L per minute), a system collection efficiency of approximately 60%, the ability to output a liquid sample (using automated sample extraction) in 0.5 to 1 mL buffer solutions (minimizing the consumption of reagents), and the ability to direct the liquid sample into an integrated third-party detection system. For some embodiments, preferred (but not limiting) design parameters for sampler 10 that is intended to output a vapor or gaseous sample include continuous autonomous operation, relatively high flow rate (up to 800 L per minute, for example, with range of about 300-400 L per minute), a system collection efficiency of approximately 60%, the ability to output a gaseous sample (using automated sample extraction), and the ability to direct the gaseous sample into an integrated third-party detection system. An optimal strategy for low vapor pressure chemical sampling will likely combine traditional vapor sampling with advanced aerosol sampling. It may also be desirable to combine low pressure drop virtual impactors with an impactor to concentrate aerosol particles into a very small area, which offers the highest potential concentration factor, and a relatively low operating cost. As discussed below, if desired, a regenerable surface technology can be implemented to enhance the operational life of the sampler.

Figure 1B:
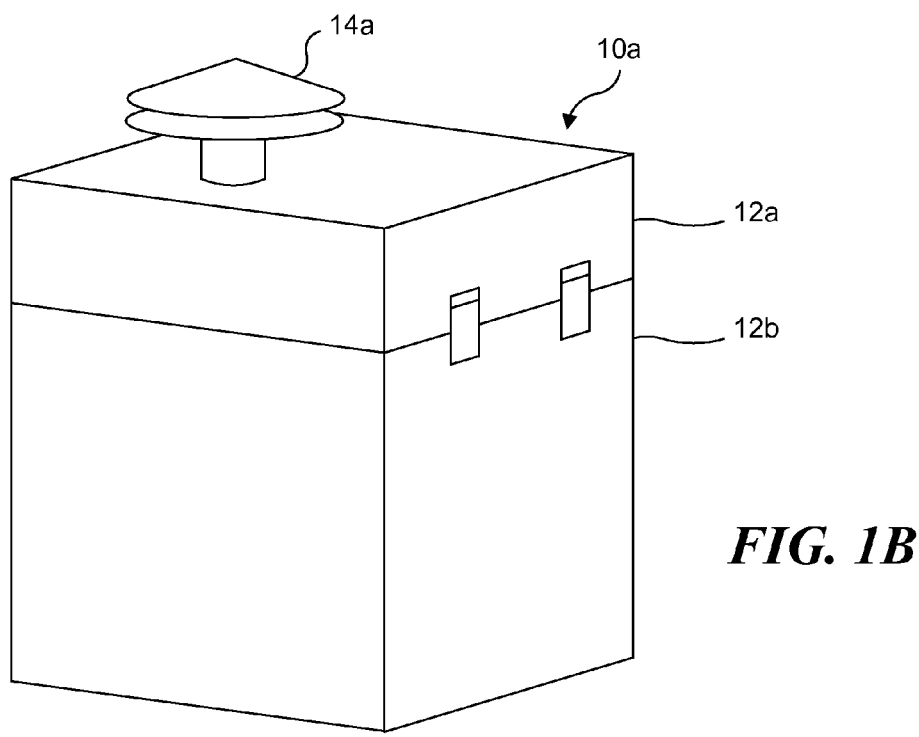

In one embodiment, schematically illustrated in FIG. 1B, a portable sampler 10a including an integrated inlet/pre-filter and two-stage concentrator is implemented. An omni-directional inlet 14a (an inertial impactor-based pre-filter; see FIG. 3A for additional detail) for outdoor sampling is coupled with a virtual impactor configured to separate large particles from small particles. Note a portion of inlet 14a extends beyond housing 12. The minor flow from the virtual impactor/concentrator is then directed to an impaction surface to generate either a spot of deposited particles or a streak of deposited particles. Such a design is suitable for fluid rates of from about 400 L per minute to about 500 L per minute. The collection efficiency exhibited by such a design is about 50%. Advantages of the design include: time delineated sample capture, automated and autonomous sample extraction from a dry sample, integration of a redundant spot for archival purposes with little marginal cost, automated and autonomous operation possible for long periods of time (in contrast with dry filters), lower sensitivity to temperature and humidity parameters, compared to cyclone-based samplers, potential for low power/low weight implementations, and a superior microbial concentration factor. Sampler 10a can include a light-weight/ impact resistant two-piece housing, with an upper portion 12a and a lower portion 12b, configured to enable easy access to internal components for maintenance and replenishment of consumables (such as wash liquids).

Figure 2:
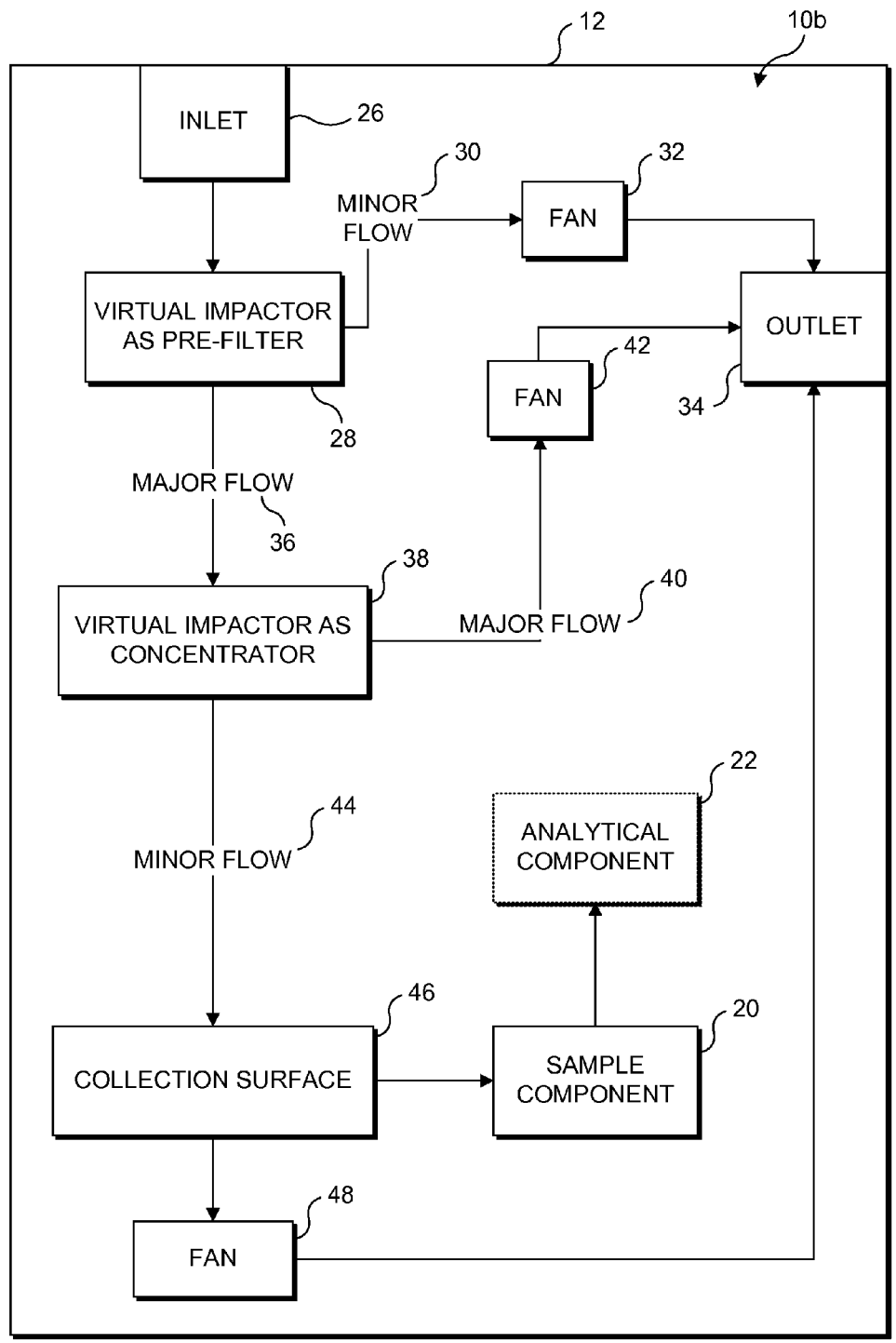

FIG. 2 is a block diagram schematically illustrating functional elements of another exemplary air sampler implementing the concepts disclosed herein. Note that sampler 10b of FIG. 2 is more detailed, and illustrates an exemplary (but not limiting) configuration of fans to move fluid through the sampler. However, the embodiment of FIG. 2 is more limited, in that the pre-filter is implemented as a virtual impactor, not as an inertial impactor or pore-based filter. Sampler 10b includes housing 12, and air inlet 26, a first virtual impactor 28 (implementing pre-filter 14 of FIG. 1A), a second virtual impactor 38 (implementing concentrator 16 of FIG. 1A), a collection surface 46 (implementing particle collector 18 of FIG. 1A), sample component 20, analysis component 22 (which can be optional if the sample is conveyed to a third-party analytical instrument; such an implementation would likely require a sample port, not separately shown, configured to be coupled to the third-party analytical instrument), a plurality of fans configured to move air throughout the air sampler, and an outlet 34 that exhausts air from the air sampler. While not specifically shown, it should be understand that structures such as flexible tubing or other conduits can be used to couple the various components in fluid communication with one another, as appropriate.

Note that virtual impactor 28 is configured to discharge minor flow 30 from the sampler via outlet 34. Those of ordinary skill in the art will readily recognized that while the pressure drop through a virtual impactor is highest at the minor flow outlet as compared to the major flow outlet, both the minor flow outlet and the major flow outlet can be coupled in fluid communication with a low-pressure source (such as a fan or pump) to draw fluid through the virtual impactor. For example, fan 32 is disposed between minor flow 30 and outlet 34, to draw air from inlet 26 through virtual impactor 28. As described in greater detail below, major flow 36 is coupled in fluid communication with other fans. While the fan could be disposed upstream of the virtual impactor to force air through the virtual impactor (providing high pressure at the inlet of the virtual impactor, such that ambient pressure corresponds to the low-pressure source), such a design is less preferred, because it increases the turbulence in the air flow and interferes with particle collection. Minor flow 30 includes a minor portion of the air that entered virtual impactor 28, and a majority of the particles larger than a cut size associated with the virtual impactor. Thus, virtual impactor 28 is acting as a filter that discards the majority of the particles larger than the cut size. Where the air sampler is designed to sample respirable particles, a particularly preferred cut size is about 10μ (although it should be recognized that such a cut size is intended to be exemplary, rather than limiting). Major flow 36 exiting virtual impactor 28 includes a majority of the air that entered virtual impactor 28, a minority of the particles larger than the cut size, and a majority of the particles smaller than the cut size. Thus, careful selection of the cut size associated with virtual impactor 28 insures most of the particles of interest are entrained within major flow 36. Note that very little concentration of the particles of interest has yet been achieved, as relatively little air has been discarded through the minor flow.

Virtual impactor 38 (which is acting as the concentrator) is disposed downstream of virtual impactor 28 (which is acting as the pre-filter), such that major flow 36 is directed into virtual impactor 38. Once again, both a major flow 40 and a minor flow 44 exit virtual impactor 38. Major flow 40 includes the majority of the air entering virtual impactor 38, and a minority of the particles larger than the cut size associated with virtual impactor 38. Major flow 40 is directed to outlet 34 via a fan 42 disposed between virtual impactor 38 and outlet 34. Those of ordinary skill in the art will readily recognize that in some embodiments a single fan can be used to implement fans 32 and 42, and it should be recognized that the present disclosure encompasses such an embodiment. The use of a plurality of fans can provide a benefit in that achieving a desired pressure balance through the air sampler can be easier if a plurality of fans are implemented. Minor flow 44 exiting virtual impactor 38 includes a minor portion of the air that entered virtual impactor 38, as well as a majority of the particles greater than the cut size associated with virtual impactor 38, thereby achieving concentration of the particles of interest by discarding a majority of the air and a majority of particles smaller than the cut size.

Collection surface 46 (implementing the particle collector of FIG. 1A) is disposed downstream of virtual impactor 38. Collection surface 46 is configured to remove particles of interest from minor flow 44. A fan 48 is disposed between collection surface 46 and outlet 34, providing a low-pressure source that draws air through the high pressure drop portion of virtual impactor 38 (i.e., minor flow 44). Having served its purpose, minor flow 44 is discharged through outlet 34 (however, it should be recognized that if desired, a separate outlet could be used). As discussed above in detail, a different specific configuration of fans (i.e., low-pressure sources, pumps, or vacuum pumps could also be implemented, and it should be recognized that such alternatives are encompassed in the present disclosure) can be employed. In some embodiments, a single fan can be employed to draw air through the air sampler, recognizing that implementation of a plurality of low-pressure sources can facilitate pressure balancing throughout the air sampler.

As discussed above in detail, sampling component 20 is configured to obtain a sample from the particles deposited upon the collection surface, and to prepare the particles for analysis by analytical component 22. The specific analytical component will determine the type of sample (i.e., dry, wet, vaporous, or gaseous) provided by sampling component 20. It should be recognized that some analysis components may not require removal of particulates from the collection surface. For example, optical detection of biological particles by stimulating their fluorescence can be achieved without removing biological particles from a collection surface. Thus, it should be recognized that the concepts disclosed herein encompass embodiments where sampling component 20 is not required. Where sampling component 20 is not required, a regeneration component may be used to clean the collection surface to facilitate collection of additional particles for subsequent analysis, without fear of contamination by the presence of previously collected particles.

Figure 3A:
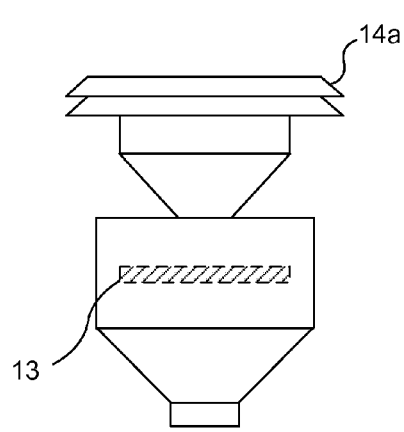

Having discussed several exemplary embodiments of air samplers in accord with the concepts disclosed herein, details relating to the three different types of pre-filters that can be beneficially employed in such air samplers will now be provided. As noted above, inertial impactors, filters including a plurality of pores, and virtual impactors can be used as pre-filters. FIG. 3A schematically illustrates an inertial impactor 14a including an impaction plate 13 that can be used to implement the pre-filter of FIG. 1A. Details relating to how impaction plates remove relatively larger particles while letting relatively smaller particles pass are discussed below in connection with the description of FIG. 4A. A potential disadvantage associated with the use of an inertial impactor as a pre-filter is that the relatively large particles that are removed from the air stream passing through the pre-filter/inertial impactor accumulate, such that over time, the removal efficiency of the inertial impactor is reduced. Eventually, the impaction plate will need to be cleaned or replaced to remove the accumulated particles. Preferably, when an inertial impactor is used as a pre-filter, the impaction plate in the inertial impactor is relatively easy to access, to enable the impaction plate to be cleaned.

Figure 3B:
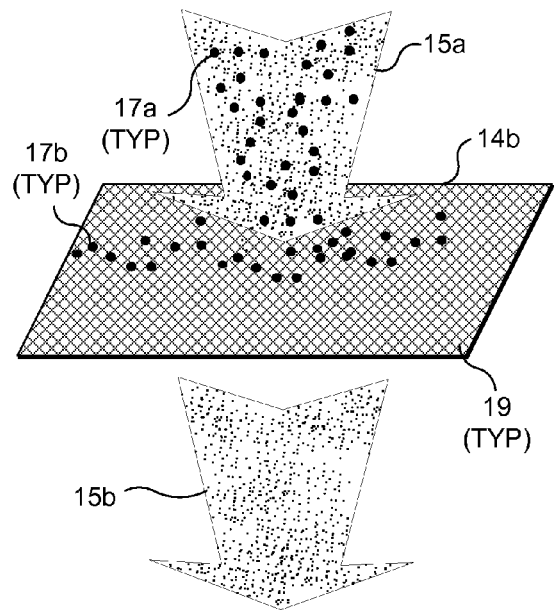

FIG. 3B schematically illustrates a filter 14b that can be used to implement the pre-filter of FIG. 1A, and which comprises a plurality of pores 19. The relative size of pores 19 is selected to be smaller than particles 17a (i.e., the oversized particles discussed above, which are larger than the particles of interest that the sampler is configured to collect). Airflow 15a includes both particles 17a and particles that are smaller than the oversized particles (the smaller particles include both the particles of interest and even smaller particles, i.e., particles that are smaller than the particles of interest). As airflow passes through the filter 14b, the oversized particles are removed, generally as indicated by particles 17b. Thus, airflow 15b, having passed through filter 14b, includes only the smaller particles, and not the oversized particles. A potential disadvantage associated with the use of a pore-based filter as a pre-filter is that the relatively large particles that are removed from the air stream passing through the pore-based filter accumulate, and over time, the pore-based filter becomes clogged and must be replaced or cleaned. When a pore-based filter is used as a pre-filter, the pore-based filter should be relatively easy to access, to facilitate replacement or cleaning of the pore-based filter.

Figure 3C:
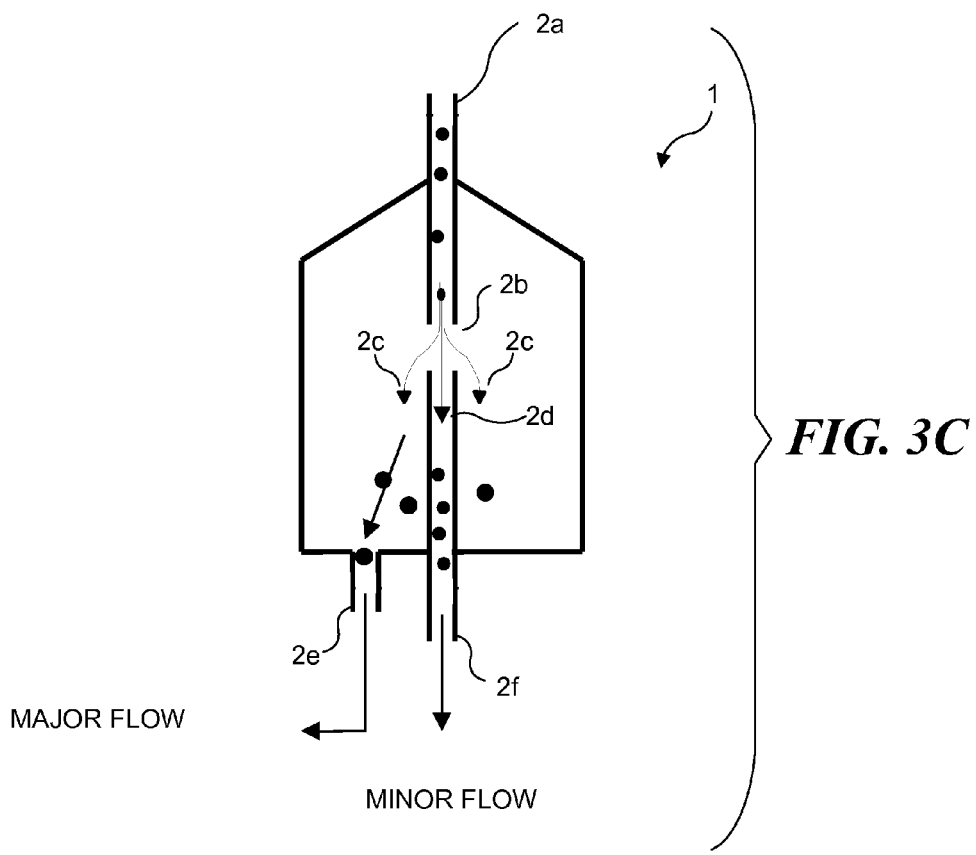

FIG. 3C schematically illustrates a virtual impactor that can be used for the pre-filter of FIG. 1A. Virtual impactors do not include an impaction surface but instead, separate a flow of gaseous fluid into two portions, i.e., a major flow including a major portion of the gaseous fluid, and a minor portion including a minor portion of the gaseous fluid. Virtual impactors can be configured such that particles of interest are concentrated in the minor flow. Thus, virtual impactors concentrate particles of interest into a designated portion of the gaseous fluid. Virtual impactors can achieve such a concentration while removing very few of the particulates of interest from the flow of gaseous fluid. As a result, the particulate-laden gaseous fluid flow can be passed through a series of sequentially or serially-connected virtual impactors, so that a gaseous fluid flow exiting the final virtual impactor has a concentration of particulates two orders of magnitude greater than in the original gaseous fluid flow. The concentrated gaseous fluid (i.e., the portion of the gaseous fluid including a larger portion of the particles of interest) can then be directed onto an impaction substrate, such that the particulates are deposited on the sample substrate in higher numbers and with greater density, or alternatively, a substantially similar number of particles can be deposited in substantially less time. Thus, virtual impactors can be used as the "nozzle" of an impactor (i.e., the portion of an impactor that directs the flow of gaseous fluid onto the impaction plate/sample substrate, although it should be recognized that a tubing or conduit can be disposed between the minor flow outlet of a virtual impactor and the impaction plate/collection surface). A virtual impactor uses a particle's inertia to separate it from a gaseous fluid stream when the direction of the stream is turned, and a basic virtual impactor can be fabricated from a pair of opposed nozzles. Within a virtual impactor, the intake gaseous fluid coming through the inlet flows out from a nozzle directly at a second opposed nozzle into which only a "minor flow" is allowed to enter. This concept is schematically illustrated by a virtual impactor 1 shown in FIG. 3C. Gaseous fluid carrying entrained particulates flows through a first nozzle 2a. The flow from nozzle 2a then passes through a void 2b that is disposed between nozzle 2a and a nozzle 2f. It is in void 2b that the flow of gaseous fluid is divided into a major flow 2c, which contains most of the gaseous fluid (e.g., 90%) carrying particles smaller than a cut (predetermined) size, and a minor flow 2d. Minor flow 2d contains a small amount of gaseous fluid (e.g., 10%) in which particulates larger than the cut size are entrained.

As a result of inertia, most of the particulates that are greater than the selected cut size are conveyed in this small minor flow and exit the virtual impactor. Most of the particulates smaller than the virtual impactor cut size are exhausted with the majority of the inlet air as the major flow. The stopping distance of a particle is an important parameter in a virtual impactor design. The cut point (size at which about 50% of the particles impact a surface, i.e., flow into the second nozzle) is related to the stopping distance. A 3 micron particle has nine times the stopping distance of a 1 micron particle of similar density.

FIG. 4A schematically illustrates an exemplary inertial impactor, wherein an air sample 3 including relatively large particles 5a and relatively small particles 5b is directed towards an impaction/collection surface 9 (preferably through a nozzle 7). As discussed in detail above, a low-pressure source can be used to draw air through the inertial impactor, over impaction/collection surface 9, which collects particles 5c having an inertia too great to follow the curved path of the air stream. Thus, the term "inertial impactor" typically refers to a unit comprising of air inlet, a spotting or acceleration nozzle, and an impaction plate. At the acceleration nozzle exit, the airstreams turns sharply, and particles larger than a certain diameter (referred to as the impactor's cut-off size) impinge on the collection surface of the impaction plate due to inertial forces. Exemplary inertial impactors are discussed in U.S. Pat. Nos. 6,435,043; 5,553,795; 5,437,198; 4,926,679; 4,796,475; 4,321,822; and 4,133,202. The physical principles of operation of an inertial impactor are similar to those of a virtual impactor, as described in detail above, except the inertial impactor includes the impaction/collection surface, whereas the virtual impactor does not.

In an exemplary, but not limiting embodiment, the air velocity through an inertial impactor is greater than about 10 m/s and less than about 100 m/s, and may be greater than about 20 m/s and less than about 30 m/s. The nozzle diameter is greater than about 0.25 mm and less than about 2.5 mm, and can be greater than about 0.5 mm and less than about 1 mm. The nozzle is located at a distance from the impaction surface greater than about 0.1 mm and less than about 2 mm, and can be at a distance greater than about 0.25 mm and less than about 0.5 mm.

In an exemplary, but not limiting embodiment, the inertial impactor is configured for optimum collection of particles in about the 0.5-10 μm diameter, and can be in the about 1 μm-5 μm range. Airborne particles in this range are the most likely to represent an inhalation hazards to humans. Within this range, bacteria would be captured, as well as potentially noxious viruses or protein aggregates. However, the inertial impactor may be configured for optimal collection of particles of other size ranges, in different applications.

FIG. 4B schematically illustrates an exemplary configuration between a virtual impactor, an impaction plate configured to act as a collection surface, and a fan that can be implemented in the air samplers disclosed herein. Referring to sampler 10b of FIG. 2, minor flow 44 is drawn past collection surface 46 by fan 48. Referring to FIG. 4B, where collection surface 46a is implemented by an inertial impactor including a single impaction surface 47a, minor flow 44a is drawn past impaction surface 47a, depositing particles larger than the cut size upon impaction surface 47a. Significantly, particles larger than the cut size of that bounce off the impaction surface are generally reintroduced into the minor flow and are not collected.

FIG. 4C schematically illustrates an exemplary configuration between a virtual impactor, a plurality of beads configured to act as a collection surface, and a fan that can be implemented in the air samplers disclosed herein. Referring to sampler 10b of FIG. 2, minor flow 44 is drawn past collection surface 46 by fan 48. Referring to FIG. 4C, where collection surface 46a is implemented by a plurality of impaction surfaces 47b (i.e., a plurality of beads), minor flow 44b is drawn past the plurality of impaction surfaces 47b, depositing particles larger than the cut size upon the plurality of impaction surfaces. Significantly, particles larger than the cut size that bounce off one of the impaction surfaces is likely to encounter another impaction surface as minor flow 44b flows through the packed beads in a circuitous fashion. Thus, particles bouncing off one impaction surface are more likely to be collected by still another impaction surface, thereby increasing the collection efficiency as compared to the use of a single impaction surface. Preferably, the plurality of impaction surfaces are significantly larger than the particles of interest. For example, beads of about 300μ in diameter can be used to collect particles of about 10μ in diameter, although such relative sizes should be considered exemplary, rather than limiting. Beads can also be as little as five to ten times the size of the particles. Smaller, more tightly packed beads are likely to generate a greater pressure drop, and if one goal is to minimize a pressure drop in the air sampler, relatively larger beads can be employed.

A sample of particles deposited in the bead bed can be removed by rinsing the bead bed with a solvent. Agitating the bead bed may facilitate sample extraction. The agitation can be implemented using ultrasonic or sonic waves, or by otherwise physically moving the bead bed. Depending on the type of particulates that have been collected, heating the bead bed may be used to obtain a gaseous or vaporous sample. Once a sample has been collected, the bead bed can be regenerated and prepared to collect additional particles by rinsing the bead bed with an aqueous solution, preferably including a surfactant. Empirical studies have shown that aqueous solutions including about 0.5% surfactants can be beneficially employed to regenerate a bead bed. The beads themselves can be implemented by generally spherical (or granular) polymer or glass beads. Inorganic substrates may also be used as well. In general the beads will be inert, although it should be recognized that any of the coatings discussed below with respect to enhancing collection efficiency can be beneficially incorporated onto one or more of the beads. In some embodiments, only some of beads in the bead bed include a coating, while in other embodiments, substantially all of the beads in the bead bed include a coating. In still other embodiments, some of the plurality of beads have been coated with a first material, while other beads have been coated with a different material. Coating different beads with different materials will facilitate collection of disparate particles, which under some circumstances, may not be desired, but which may be desirable in other sampling paradigms. In general, deeper bead beds will have better collection efficiencies. In at least one embodiment, the bead bed is about 50 beads deep, although this bead depth is intended to be exemplary, rather than limiting.

For the air samplers described herein, several types of virtual impactor and impactor combinations are suitable for use in collecting samples of particles as spots on a substrate. As noted above, concentrating particles deposited on an impaction surface as the spot facilitates subsequent collection of a sample. Because the specific design of the inertial impactor (including a nozzle directing the airflow towards the impaction surface) can be optimized for a particular size of particles, it is contemplated that at least some embodiments disclosed herein may include multiple nozzles, each with a different geometry, so that multiple particle types can be efficiently collected.

In an exemplary embodiment, the nozzle directing the gaseous fluid toward the impaction plate/sample substrate is a spotting nozzle. The spotting nozzle receives a gaseous fluid from an inlet, accelerates the gaseous fluid within the nozzle body, and discharges the accelerated fluid through an outlet. The spotting nozzle thus directs a jet of accelerated gaseous fluid toward the impaction plate. The spotting nozzle increases the mean velocity of the gaseous fluid to provide sufficient momentum to particles above a specific size so that such particles are able to impact and be retained upon the impaction plate/sample substrate. For example, a gaseous fluid sample may be sucked through a nozzle having a reduced cross-sectional area relative to a source of gas using a downstream vacuum pump. The spotting nozzle is preferably configured to deposit a spot of particles onto the impaction plate/sample substrate. The term "spot" as used herein is intended to represent an aggregate of particulates or particles deposited upon a substrate in a relatively small area, such that the spot region has relatively high numbers of particles on the substrate in the spot area and the area outside the spot includes substantially fewer particles (or none) on the substrate, i.e., a spot, a relatively dense group of particles which can be more readily observed by magnification, with the unaided eye, or using other detection techniques.

Preferably, the intake of the spotting nozzle is downstream of a virtual impactor, such that the gaseous fluid accelerated by the spotting nozzle is concentrated with respect to the particles entrained within the gaseous fluid. The term "downstream" is intended to indicate that the spotting nozzle and the virtual impactor are configured so that the gaseous fluid passes first through the virtual impactor, and then through the spotting nozzle. As discussed above, a virtual impactor is an apparatus that increases the concentration of airborne particles of a desirable size range. It separates an airflow into a minor and a major component, wherein the minor component carries a majority of airborne particles above a certain size. Examples of virtual impactors can be found in U.S. patent application Ser. No. 09/955,481, or in U.S. Pat. Nos. 3,901,798; 4,670,135; 4,767,524; 5,425,802; and 5,533,406. Thus, the spotting nozzle can be downstream of the minor flow of a virtual impactor. The virtual impactor can increase the concentration of particles that are above about 1 μm in size. In some embodiments, more than one virtual impactor can be placed upstream of the spotting nozzle. Impacting air with higher concentration of airborne particles in the desired range increases the collection pace and thus, the efficiency or sensitivity of this novel device. It should be recognized at the spotting nozzle in the outlet of the virtual impactor may be separated by some distance. Flexible tubing, hose, or some other type of conduit can be used to couple the outlet of the virtual impactor to the spotting nozzle. Preferably, the spotting nozzle is disposed adjacent to the collection surface.

In one preferred embodiment, two virtual impactors are connected in series, such that a concentration of particulates entrained in the minor flow of gaseous fluid exiting the second virtual impactor is approximately 70 times the original concentration.

Figure 4D:
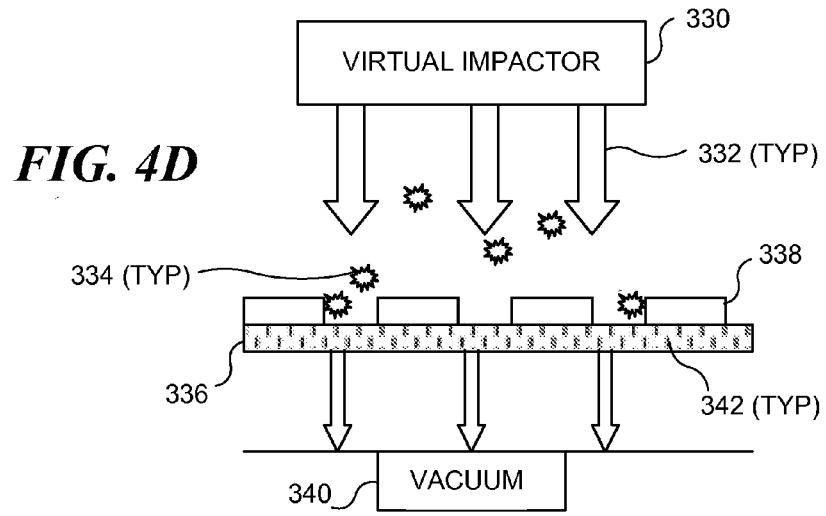
Figure 5:
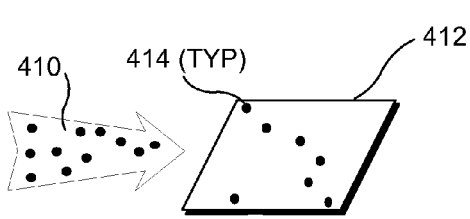
FIG. 5 (prior art) is a schematic view of a fluid in which particulates are entrained, showing the particulates impacting an uncoated impact collection surface.
Figure 6A:
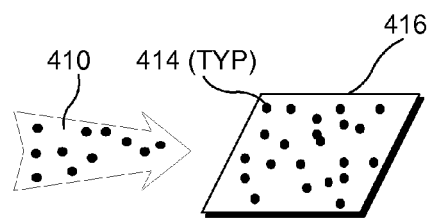
FIG. 6A is a schematic view of a fluid in which particulates are entrained, showing the particulates impacting a coated impact collection surface in accord with one aspect of the concepts disclosed herein.
Figure 6B:
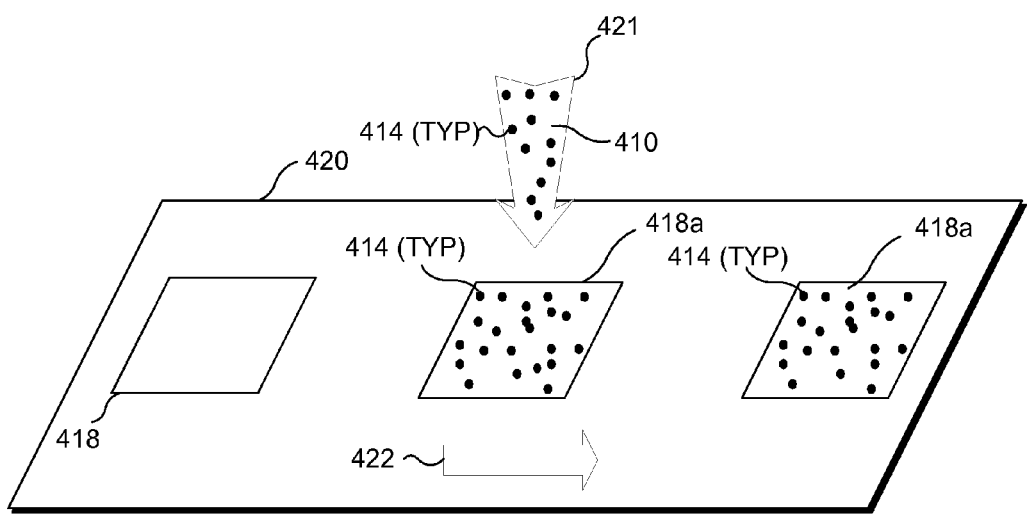
FIG. 6B is a schematic view of a flexible tape having a partially coated impact collection surface.

FIG. 4D schematically illustrates an exemplary configuration disposed between a virtual impactor, a porous substrate configured to act as a collection surface, and a vacuum pump (or other source of reduced pressure) that can be implemented in the air samplers disclosed herein. A minor flow 332 from a virtual impactor 330 is conveyed (either directly, through a spotting nozzle, or through flexible tubing or some other conduit, or some combination thereof) to a porous hydrophilic filter medium 336, which serves as the impaction/collection surface. Preferably a hydrophobic material 338 would be deposited over porous hydrophilic filter medium 336. Openings 342 in hydrophobic material 338 direct particulates 334 entrained in minor flow 332 toward locations on porous hydrophilic filter medium 336 on which the particulates will be collected. The fluid in which the particulates are entrained passes through the porous hydrophilic filter medium 336, leaving the particulates deposited on the surface. A vacuum source 340 (or fan or other low-pressure source generally as described above) can be beneficially employed to ensure that the minor flow fluid passes through the porous filter, rather than being diverted around the sides of the porous filter. The area between the introduction of the minor flow and the filter can be sealed, so the particulates will not be lost prior to impact. The sealing can extend between the bottom of the porous filter and vacuum source 340.

As shown in FIG. 4D, the minor flow is directed towards the collection surface as three separate streams. It should be understood that either fewer or more than three minor flow streams could alternatively be employed as well. The benefit of employing multiple minor flows is that individual virtual impactors can be fabricated to selectively direct particulates of a desired size into the minor flow. Thus, by employing a plurality of virtual impactors, each concentrating a different particulate size into their respective minor flows, particulates of different sizes can be directed onto different locations of a collection surface. Alternately, particulates of the same size can be deposited in different locations, permitting duplication of sampling to occur, to facilitate multiple testing, perhaps at different times, or to save a portion of the simultaneously collected particulates for archival purposes while analyzing another portion of the simultaneously collected particulates.

Note that in FIG. 4D, a surface coating or layer has been applied over the collection surface to define receptacles for spots. Such a coating (hydrophobic material 338) is not required, but is a useful addition. Regardless of whether a porous or non-porous collection surface is employed, several different surface treatments may be useful in increasing the efficiency of spot formation. For example, a common problem with surface impaction is that particles bounce off the surface, return to the fluid stream, and are swept away. This problem can be reduced by coating the surface to promote particle adhesion. Such surface coatings include, but are not limited to, charged chemical species, proteins, and viscous substances that increase the impact force required to enable the particulates to bounce away from the collection surface. Details of exemplary coatings that can be beneficially employed in air samplers in accord with the concepts disclosed herein are described below. It should be noted that a person skilled in the art will recognize that many other coatings, having other physical and chemical properties, can be beneficially employed to aid in the collection of specific types of particulates. In at least one embodiment, the coating is on the order of 100 microns thick, while the collection surface itself is on the order of 100 millimeters thick.

It should be noted that the collection surface, with or without a coating, need not be flat. For example, a surface with portions raised significantly above the bulk of the surface can also be used to collect spots of particulates. Thus, a textured surface with portions raised substantially above a background portion of the surface can be used to collect spots of particulates. Such textured surfaces are disclosed in commonly assigned U.S. Pat. No. 6,110,247, the disclosure and drawings of which are hereby specifically incorporated herein by reference. Such surfaces reduce the tendency of particles to bounce and therefore increase spot formation efficiency.

Surface Coatings for Collection/Impaction Surfaces: FIGS. 5 and 6A-6C schematically illustrate how coating an impact collection surface, with a material can substantially enhance the efficiency of that surface. FIG. 5 shows a fluid 410 in which particulates 414 are entrained, moving relative to a (prior art) impact collection surface 412 that is not coated. Particulates 414 are separated from the fluid by striking against impact collection surface 412. FIG. 6A shows fluid 410 moving toward a coated impact collection surface 416, which has been coated with a material that retains substantially more of the particulates entrained in fluid 410 than would an uncoated surface. By comparing FIGS. 5 and 6A, it will be apparent that substantially more particulates 414 are collected on coated impact collection surface 416 than on impact collection surface 412.

The relatively greater density of particulates 414 evident on coated impact collection surface 416, compared to impact collection surface 412, is due to a characteristic of the coating that causes it to better retain particulates and thus more efficiently separate the particulates from the fluid in which they are entrained, compared to the prior art impact collection surface that is not coated. In the embodiment shown in FIG. 6A, the geometry of impact collection surface 416 is generally irrelevant. The coating disclosed herein can be applied to the impact collection surfaces in almost any impact collector or virtual impact collector. Simply by coating surfaces on which a stream of particles impacts with one of the materials described below, a substantial increase in the efficiency with which the particulates are separated from a fluid and collected is achieved.

FIG. 6B schematically illustrates an embodiment in which a plurality of coated areas 418 are applied to an upper exposed surface of an elongate tape 420. As illustrated in this Figure, tape 420 is advanced from left to right, i.e., in the direction indicated by an arrow 422. Tape 420 thus moves past a stream 421 of fluid 410 in which particulates 414 are entrained. Stream 421 is directed toward the upper surface of the tape. As the tape advances, fresh coated areas 418 are exposed to impact by particulates 414. The particulates that impact on these coated areas are at least initially retained thereon, as shown in coated areas 418*a*. In the embodiment illustrated in FIG. 6B, coated areas 418 and 418*a* are not contiguous, but instead are discrete patches disposed in a spaced-apart array along the longitudinal axis of tape 420. Various types of materials described below can be used to produce coated areas 418.

In an alternative exemplary embodiment shown in FIG. 6C, a continuous coated impact collection surface 423 extends longitudinally along the center of a tape 420*a*. As tape 420*a* advances in the direction indicated by arrow 422, stream 421 of fluid 410 with entrained particulates 414 is directed toward the upper surface of the tape. Particulates 414 are retained by the coating, as shown in a coated impact collection surface 423*a*. As tape 420*a* advances in direction 422, coated impact collection surface 423 is exposed to impact by particulates 414 carried in stream 421. In the embodiment that is illustrated, the coating does not cover the entire upper surface of tape 420*a*. However, it should be understood that any portion or the entire upper surface of tape 420*a* can be covered with the coating.

The material used for producing coated impact collection surface 423 and other coated areas or surfaces employed in this description for collecting particulates in accord with the concepts disclosed herein, is selected based upon certain characteristics of the material that increase the efficiency with which the particulates are separated from the fluid in which they are entrained. Each material used for a coating has certain advantages that may make it preferable compared to other materials for separating a specific type of particulate from a specific type of fluid. For example, for use in collecting particulates in dry air or other dry fluid, a material called TETRAGLYME can be used for the coating. This material is hydrophilic until it is exposed to water and when dry, is relatively very sticky, tending to readily retain particulates that impact it. However, once water is sprayed onto the TETRAGLYME coated surface so that it is wetted, the coating becomes hydrophobic. When hydrophobic, the TETRAGLYME coated surface is no longer sticky or tacky, and in fact, readily releases the particulates that previously were retained by it. The water (or other liquid containing water) easily washes the particulates away from the coated impact collection surface. TETRAGLYME, which is available from a number of chemical supply houses, is bis(2-[methoxyethoxy] ethyl)ether tetraethylene glycol dimethyl ether dimethoxy tetraethylene glycol and has the formula: $CH_3OCH_2(CH_2OCH_2)_3$ $CH_2OCH_3$ $CH_3—O—CH_2—CH_2—O—CH_2—CH_2—O—CH_2—CH_2—O—CH_2—CH_2—O—CH_3$. Tests have shown that TETRAGLYME coating can collect more than three times as many particulates as an uncoated surface. Water molecules are retained by the molecule by links to the oxygen atoms, as shown below.

$$O:H_2O:O$$

A second type of material usable for a coated particulate collection surface is PARYLENE, which is a tetrafluoromore manufactured and sold by DuPont Chemical Company under the trademark INSUL-COTE™, Type N. The PARYLENE material is characterized by a relatively low coefficient of friction, causing it to be extremely slippery and not sticky. Accordingly, particulates impacting against a coated surface comprising PARYLENE are initially separated from the fluid in which they are carried by the impact with the coated surface and are initially retained by the coated surface. However, these particulates are readily washed away from the PARYLENE coated surface by water or other liquid sprayed onto the coating. The particulates retained by a PARYLENE coated surface on tape 420*a* are readily washed away from the coating by water or other liquid spray.

The TETRAGLYME material is an example of a class of materials that has two distinct states related to particulate collection. When dry and hydrophilic, the TETRAGLYME material is in a first state, in which it is sticky and is very efficient at separating particulates from the fluid in which they are entrained, compared to an uncoated surface. However, when wetted, the TETRAGLYME material changes to its second state, in which it readily releases the particulates.

As shown in FIG. 7, a mono-layer material 476 can be applied to a surface 474 of a particulate collector to separate specific biological particulates 472 from a fluid 468 such as air or a liquid in which they are entrained. It is contemplated that the fluid conveying the biological particulates may also include blood. A stream 470 of the biological particulates is directed at material 476, so that the biological particulates impact thereon. Mono-layer material 476 comprises a plurality of antibodies 478 that are selected to link with the antigens on biological particulates 472. For example, if biological particulates 472 comprise anthrax spores, and if antibodies 478 are selected that are specific to anthrax spores, the anthrax spores will be readily separated and retained by linking with the antibodies on the coating. These anthrax spores may then be identified based upon an appropriate analysis. The type of analysis employed is outside the scope of this disclosure. Those of ordinary skill in the art will recognize that based on the nature of the targeted particulates, a specific analytical procedure may be more or less appropriate.

It is also contemplated that the coated impact collection surface need not be planar. Indeed, it is likely that enhanced particulate collection efficiency can be achieved by using a non-planar coated surface to collect particulates. FIG. 8A illustrates an enlarged view of a portion of one preferred embodiment for a textured particulate collection surface 490 having a plurality of outwardly projecting rods 492 distributed thereon. The outwardly projecting rods increase the surface area of particulate collection surface 490, which is provided with a coating 494 of one of the coating materials discussed above, and also increase the "roughness" of the surface to further enhance the collection efficiency of the coating. Coating 494 may be applied over rods 492 or applied before the rods are attached. Alternatively, other projecting structures such as ribs 496 may be employed on textured particulate collection surface 490, as shown in FIG. 8B.

In at least one embodiment, the collection surface incorporates a material that helps maintain the particulates deposited on the collection surface in good condition, without substantial degradation. For some particles, such as living cells, this material may be a liquid that contains nutrients. Applying a hydrogel or equivalent coating on the collection surface would allow localization of water. The water can be used to deliver salts, sugars, proteins, and other nutrients to enable the cells to survive on the collection surface during the time interval between deposition on the collection surface and subsequent analysis of the collected samples of particulates.

For all of the collection surfaces noted above, some portion of the analysis/detection scheme could be included as part of the surface. For example, if the analysis employed to detect a specific particulate involves incubating the collected particulates (some of which are likely to be bioparticles) with a reagent, the reagent can be incorporated onto the surface so that the incubation period is initiated upon deposition.

Sampling Component: As discussed above, particularly preferred air samplers in accord with the concepts disclosed herein beneficially incorporate a sampling component configured to remove at least a portion of the particles deposited upon the collection surface such that a sample of particles can be conveyed to an analytical component for analysis. The types of particles the air sampler has been designed to collect will play a significant role in determining the type of analytical component that will be used to analyze the particles, and the type of sampling component required to obtain the necessary sample. For example, some analytical components require dry samples, some require liquid samples, and still others require gaseous samples. The specific sampling component implemented will be configured to provide a sample required for a specific analytical component. FIGS. 9A-9E, 10, 11A, 11B, 12A, 12B, 13, 14, 15A, 15B, and 16 specifically refer to various exemplary sampling component embodiments encompassed within the concepts disclosed herein.

With respect to sampling components configured to provide a liquid sample, the sampling component will need to incorporate a liquid rinse supply volume configured to store a volume of liquid to be used to generate a liquid sample. The liquid can be an organic solvent or an aqueous solution (such as saline). The specific liquid employed should be selected based on the analytical component implemented (because some liquids may be incompatible with certain analytical techniques), as well as the type of particle being sampled (and because some liquids may be incompatible with specific types of particles; if the particles are biological in nature, and the analytical technique requires the biological particles be alive, then liquids toxic to the biological particles cannot be employed). A liquid sample can be prepared by rinsing the collection surface with the liquid to remove the particles, using some other mechanism (such as a mechanical scraper or a jet of compressed air) to dislodge particles that are then introduced into the liquid, or by removing a portion of the collection surface and introducing that portion into a volume of the liquid (or some combination thereof). The use of relatively small volumes (i.e., on the order of milliliters or less, although it should be recognized that such a metric is intended to be exemplary, rather than limiting) of liquid to prepare the liquid sample provides several benefits. First, the smaller the volume of liquid, the more concentrated the particles that will be in the sample, generally facilitating the analysis. Second, using relatively small volumes of liquid to generate each sample will reduce the liquid supply that needs to be incorporated into the air sampler, which enables smaller, more compact, and more readily portable air samplers to be achieved.

FIGS. 9A-9E describe an embodiment in which simultaneously collected particles are deposited upon two distinct collection surfaces, such that one set of particles can be sampled for immediate analysis, while another set of particles can be retained for archival purposes (i.e., to be analyzed at a later date). The technique of collecting a second archival set of particles does not need to be implemented into each air sampler in accord with the concepts disclosed herein, but can be beneficially incorporated into air samplers as desired. In addition to incorporating the virtual impactor/concentrator, collection surface, and sampling component of FIGS. 1A and 2, air samplers corresponding to FIGS. 9A-9E can be configured to only convey the minor flow to an impaction/collection surface when triggered to do so (for example, the minor flow will only convey to an impaction/collection surface when a particle count reaches a predetermined level, or according to the elapse of a predefined time period), as opposed to continuously collecting particles. For example, a valve or bypass can be disposed between the virtual impactor implementing the concentrator and the impaction surface to prevent the minor flow from being placed in fluid communication with the impaction surface until triggered to do so. It should be recognized that while such embodiments are encompassed in the concepts disclosed herein, air samplers encompassed by the present disclosure need not be configured to collect particles according to such a trigger. Furthermore, it should be recognized that not every element incorporated into the air samplers of FIGS. 9A-9E need be implemented in air samplers consistent with those shown in FIGS. 1A and 2. The sampling components incorporated into the air samplers of FIGS. 9A-9E clearly can be beneficially incorporated into samplers consistent with those shown in FIGS. 1A and 2. In selected exemplary embodiments, additional elements shown in FIGS. 9A-9E, such as control elements, and prime movers may also be beneficially incorporated into samplers consistent with those shown in FIGS. 1A and 2.

One exemplary embodiment of an automated system that automatically changes collection surfaces when triggered to do so (or according to a pre-programmed schedule) includes a plurality of tickets. This Indexed Particle Collection System (IPCS) allows multiple samples to be taken without user intervention. Unused collection tickets are stored in a "magazine." When a new sample is needed, the indexed system automatically removes a new collection ticket from the fresh magazine and places it in position for sample collection. When the sample is complete, the collected sample is moved into a spent magazine and a fresh ticket is placed into position for collection of the next sample. In a prototype unit, up to 24 sample tickets fit in a magazine. Samples can be changed on a pre-programmed time interval or by a trigger signal.

FIG. 9A shows a plan view of an exemplary ticket 900, which preferably includes two collection areas, defined by raised lips 906. In a prototype unit, ticket 900 was fabricated from metal, although other durable materials, such as plastics and other polymers, can be employed. If tickets are to be reused, they should be fabricated from a material that is easy to sterilize, to avoid cross contamination. Inside each lip 906 is disposed a generally flat surface 904. Generally in the center of each flat surface 904 is an opening 902. A disposable impact surface 908 is placed inside each raised lip 906. In FIGS. 9A-9C, only one impact surface 908 is shown; however, it should be understood that each ticket can include two impact surfaces. While both impact surfaces can be analyzed, it is contemplated that a useful sampling protocol will call for one impact surface to undergo analysis and one impact surface to be archived. As has been generally discussed above, each impact surface is disposed in fluid communication with a minor flow path from a virtual impact collector. Since each ticket includes two collection areas, ticket 900 is designed to be employed in a system whose virtual impactor provides two minor flows, spaced apart, so that each minor flow is generally directed toward flat surfaces 904, upon which an impact surface will be placed. Also as discussed above, the minor flow can be configured to deposit small spots of particles on the impact surfaces.

FIG. 9B is a bottom view of exemplary ticket 900, again showing only a single impact surface 908. Lips 906 are not present on the bottom of the ticket. A logo 910 is included, to provide a reference to ensure that tickets are loaded in the proper orientation. FIG. 9C is a side view of exemplary ticket 900, again showing only a single impact surface 908. One or both of the impact surfaces are removed from the ticket and placed in a sample container 914. A punch 912 or rod can be employed to facilitate the removal of impact surface 908 from ticket 900. Openings 902 provide access to push the collection surface out of the ticket into the vial to recover the sample. The ticket design gives two parallel samples that can be removed separately, allowing one to be analyzed and one kept in reserve, or allowing parallel collection and/or analysis to be done.

FIG. 9D illustrates a prototype system for using tickets 900. System 915 (e.g., enclosed in a housing 930) includes a fluid inlet 916 that diverts a portion of a flow of fluid into system 915. Not separately shown is a fan, which is included to force fluid through system 915. As generally described above, the virtual impactors used in the air samplers disclosed herein separate a flow of fluid into minor and major flows. A virtual impactor 918 separates the fluid into a major flow 920 that can be directed to a chemical sensor, and a minor flow 922 that passes through an optical cell. The optical cell in the prototype employed a laser-based particle counter, which triggered sample collection when the level of particles in the minor flow reached a predefined threshold. It should be understood that other parameters, such as elapsed time, could also be used to trigger a sample collection.

To collect a sample, a ticket is loaded into a collection zone 924 from a fresh magazine 926. Once the sample is collected, the ticked is moved to a spent magazine 928, and a new ticket is placed into the collection zone from fresh magazine 926. While not separately shown, it should be understood that a prime mover is employed to move the tickets from the fresh magazine to the collection zone, and then to the spent magazine. Each impact surface 908 of the tickets can incorporate any of the coatings discussed above, or no coating. Each impact surface on a ticket can be provided with the same coating, particularly if one impact surface will be archived. Of course, in some collection strategies, such as when comparing the collection efficiency of one coating to another, different coatings can be employed. System 915 does not incorporate any rinsing of the sample to produce a liquid sample, but rather is intended for use in applications where the samples would be returned to a laboratory for analysis.

General Rinse System Concept: While system 915 is quite useful for collecting dry samples for later analysis or archiving, many analytical techniques require samples in liquid form. One way to include such functionality would be to provide a rinsing module as a separate, add-on module to a sampling system, as indicated by module 932 in FIG. 9D. Such a module could interface with system 915 in a minimal way, such that when a liquid sample is required, the corresponding ticket is transferred from the either the collection zone or the spent magazine to rinse means 934 in the rinse module. Such rinse means are described in more detail below. Such a modular system enables design improvements to be made incrementally to either the collection system or the rinse system, without affecting the other module. Another option would be to integrate the sample collection and rinsing into a single unit, generally as indicated in FIGS. 1A and 2. Rinse means 934 will produce a liquid sample 936, which can then be taken to a laboratory, or more preferably, be analyzed in an onboard analytical unit 938.

The basic steps of the rinsing preferably include: (1) receiving a signal to rinse a collected sample; (2) removing the appropriate ticket from either the collection zone or the spent magazine; (3) delivering the appropriate ticket to the rinse module; (4) applying a rinse liquid to the ticket in the rinse module; (5) agitating or otherwise performing steps to facilitate removal of material from the ticket in the rinse module and into the liquid to produce a liquid sample; (6) delivering the liquid sample to a sample vial; and, (7) delivering the required liquid sample volume from the sample vial to the analysis system.

One variation would be to include the step of removing only the portion of the collection surface on the ticket that contains the spot of impacted particles, which will minimize the rinse volume required to remove the particles. Such minimal removal may correspond to a physical removal (or "punching out") of the impaction spot. Conversely, such minimal removal can be achieved using means (such as a sample tube that is brought in contact with, or immediately adjacent to, the surface of the ticket) that isolates the spot and minimizes the rinse area to be rinsed.

It is contemplated that a target rinse volume would result in the collection of 1 millimeter or less of fluid sample. It is also expected that not all samples collected in the field will need to be rinsed in the field. The rinsing can be performed based on a predefined trigger event, an external input, or based on some predefined schedule. Most often, such a trigger event will cause the system to collect a liquid sample from the ticket in the collection zone. However, it would be useful to include the ability to collect a liquid sample from a previously used ticket stored in the spent magazine. Such an ability would be useful, but is not required. Arrows in FIG. 9D indicate the ticket is obtained from either the collection zone or the spent magazine.

There are a number of technological features and techniques that can be used to improve both the efficiency of the particle impaction process as well as the efficiency of particle removal after impaction. These features include the following:

Use of a porous impaction surface: in traditional impactors, the surface is solid, causing the air directed towards the surface to diverge tangentially. The air retains some portion of particles, meaning that this fraction fails to impact on the surface. If the impactor surface contains very small pores, some or all of the airflow passes directly through the surface, retaining those particles that would otherwise be lost in a traditional impactor. To be effective, the pores must either be smaller than the desired particle size, or the material must contain some other means for capturing the particles as they pass by (such as an electrostatic charge).

Use of a dissolvable impaction surface: after particles are impacted, their collection can be assisted by use of a dissolvable impaction surface. Ideally, the surface is comprised of a substance that is tolerable in the resultant liquid sample, or can be easily removed from the liquid sample. An example of a tolerable substance is cellulose, which can be formed into an impaction surface and then dissolved by exposure to the enzyme cellulase. Whether any particular substance is tolerable or easily removable depends on the specific particles of interest, as well as intended methods of analysis. The surface structures illustrated in FIGS. 8A and 8B could be formed of a soluble material. Such an impact collection surface could be fabricated into a long strip, which is moved into place for collection, then moved to the next position for rinsing (by dissolving the structures or a coating on the structures). Chitosan (which breaks down in the presence of a specific solution) and aerogels are examples of such materials, in addition to the materials discussed in greater detail above.

Dissolution of surface by other methods: it is also possible to use surfaces or surface layers that lose structural integrity when exposed to other conditions, such as ultraviolet light (e.g., depolymerization), heat, acoustics, magnetic fields, electric fields, or other phenomena. For example, a collection surface could be charged to include an electrostatic field, thereby collecting particles having an opposing charge. Reversing the polarity of the applied field would repel the collected particles. Polonium or other materials can be used to apply a charge to the particles before they impact the collection surface to facilitate such electrostatic collection/repulsion. Depending on the ambient temperatures where the system is to be used, the collection surface could be a frozen or semi-frozen impaction surface that is melted to obtain the sample. Similarly, a material having a relatively low melting point could be used either as the entire impact surface, or a coating on the impact surface. Upon the application of heat, the surface or coating would melt and flow into a sample vial, along with the sample. Such a material must be either readily removable from the sample, or must not interfere with the analysis to be employed. Filters or absorbents can be used to remove some types of unwanted material.

Use of a removable surface coating: the particles may also be efficiently rinsed if a layer on top of the surface is removable. The simplest such example is a dissolvable coating, such as a sugar layer. Another possibility is a surface coating that is held initially by a chemical bond that is later broken. One such example is a layer of streptavidin that is chemically bonded to a layer of biotin, which is covalently attached to the surface. If the rinse fluid contains excess biotin, the streptavidin will release from the surface. Many other such scenarios are possible, using other known types of materials for the surface coating. A viscous coating can be used, which when heated or cut with a thinner flows easily, enabling the coating to be poured into a sample container.

Continuous surface rinse: use of a continuous process that immediately removes impacted particles. One example is a liquid jet directed at the impaction region. Another example involves the use of a continuous layer of water run across the impaction surface. In another exemplary embodiment, the surface itself can be rotated or translated such that newly-impacted particles become wetted and rinsed, perhaps with the aid of ultrasonics, vibration, or dissolving coatings. A number of other scenarios are possible that employ other types of surface coatings. One waterfall approach involves continually pumping fluid over a surface toward which a fluid jet is directed. In such continually rinsing embodiments, the rinse fluid can be continuously collected and re-circulated.

Use of an impaction surface with protrusions or roughness: use of surface roughness, such as impaction microstructures, will enhance the collection efficiency of particle impaction by providing an additional filtering effect. In addition, the surface features may be removable or dissolvable in order to aid in particle recovery. As noted above, FIGS. 8A and 8B are exemplary of such microstructures.

Use of a live impaction surface: use of a surface that can be deformed, flexed, twisted, or vibrated to facilitate the removal of a sample, which can be done either in conjunction with a rinse fluid, or in the absence of a rinse fluid. One variation on such a live impaction surface involves a "balloon" type impaction surface, which is inflated such that the surface area of the balloon increases for sample collection, and then decreases as the balloon is deflated for rinsing. The deflated balloon has a smaller surface area, so that less fluid is required for rinsing, and the bond between the impacted particles and the balloon's surface is disturbed by the deflation process, requiring less force to remove the particles. An inflated balloon can be coated with a material that tends to flake off the surface of the balloon when the balloon is deflated. Such a material coating would likely be relatively inflexible, such that the change in the balloon's size during deflation causes the coating to fracture. Sugar based coatings, and other materials that tend to form crystalline lattice structures (such as salts) are useful in such an application. Conversely, a partially deflated balloon might be inflated to cause the coating to break away from the balloon surface.

Use of extended collection times: the time the impact surface is exposed to the minor flow can be extended, thereby accumulating larger spots that would tend to agglomerate into particles, making them larger and stickier, and thus easier to collect.

Soaking or dipping the collection surface: use of a bath of rinse fluid into which the collection surface, or a portion thereof, is repeatedly dipped, or placed for an extended period, which could be particularly useful if the collection surface includes a plurality of structures. Consider a plurality of elongate, "flagellating" strips whipping around in the minor flow to collect sample, which are then dissolved into or rinsed off by placing them into a fluid bath (like rinsing a mop).

Incorporating analytical reagents into collection surface: use of a test strip as the collection surface. Such test strips generally include one or more reagents, which must be exposed to a "developing" solution to complete the analysis. Instead of rinsing such a collection surface to obtain a sample, the collection surface is exposed to the developer, and the collection surface itself provides an indication (for example, a color change) as to whether a suspected particulate is present.

Use of an inert rinse fluid: preferably the rinse fluid will be inert, unless a specific rinse fluid is required to dissolve a coating, or required for some other functionality described above. Jets of fluid can be used to remove the impacted particles.

Manipulate the orientation of the collection surface to the minor flow: in general, the collection surface (i.e., the impact surface) will be disposed so that it is substantially normal (i.e., perpendicular) to the direction of the minor flow. Orienting the minor flow to be parallel to a collection surface would result in the particles entrained in the minor flow settling out onto the collection surface as a function of the mass of the particles. Such a surface could be periodically rinsed, and sub portions of the surface relating to specific particle masses, or a range of particle masses, could be individually rinsed away from the surface.

Use of a wiper blade: either in conjunction with the use of a rinse fluid, or alone, a blade can be used to remove collected particulates. A "windshield wiper" approach corresponds to the use of a liquid sprayed onto the collection surface and a physical blade being used to wipe off the particles.

Use of a large volume rinse: a large volume of rinse fluid can be used to remove the particles, and collected into a sample container. The large volume of fluid can be subsequently reduced (such as by evaporation), or the sample container can include binding targets, to which specific particles will bind to (such as the antibody/antigen binding discussed in connection with FIG. 7).

Incorporation of colormetric detection: Colormetric detection can be incorporated into many of the above scenarios, such that the presence of a target particle will be indicated by a color change. While such color changes are primarily qualitative, they provide a rapid and easily recognizable means to indicate if fluid samples include some level of target particles.

Combination of a movable collection surface (or minor flow nozzle) and a fluid rinse or bath: The nozzle of the minor flow could impact onto a disk shaped impact collection surface, which would slowly rotate so that the impact collection surface is immersed into a bath where soaking, vibration, dissolvable coatings or an individual one of, or a combination of the above disclosed techniques is employed to procure a liquid sample. This technique could be implemented as a continually rotating/rinsing embodiment, or as a batch rinse embodiment. Instead of a disk, a strip of material could be used with a "reel to reel" type configuration where the strip is fed into a collection area, then through a rinse chamber, and then onto a "take up reel"

It is contemplated that some embodiments of rinsing systems will beneficially incorporate combinations of the various methods discussed above. Having now discussed rinsing in general, specific examples will be provided, along with other sample retrieval techniques (i.e., non-liquid based retrieval).

An Exemplary Air Sampler with Means for Removing and Transferring Particulates from a Collection Surface to a Container: FIG. 9E illustrates an exemplary air sampler 530, for collecting and archiving particulates entrained in a flow of fluid. Such particulates can include chemical and biological compounds. System 530 (preferably enclosed in a housing 548) includes a fluid inlet 531 that diverts a portion of a flow of fluid into system 530. A fan 533, which can be centrifugal fan or an axial fan driven by a motor or other prime mover, forces fluid through system 530. It should be noted that the virtual impactors used in the air samplers disclosed herein to separate a flow of fluid into minor and major flows function best when the fluid passes through the virtual impactor at about a predefined velocity. While a source of some fluid streams may have sufficient velocity to pass through a virtual impactor without requiring a fan to drive them through the virtual impactor, it is contemplated that many applications of system 530 (such as collecting particulates from a smokestack) will require fan 533. While as shown, fan 533 forces a fluid into system 530, those of ordinary skill in the art will recognize that the fan could alternatively be positioned to draw fluid through system 530, so that the major flow through system 530 is drawn through an exhaust 535 and the fluid comprising the minor flow (after the particulates are deposited on the collection surface), exits through another port (not shown). System 530 also includes a virtual impactor 532 adapted to separate the fluid into a major flow and a minor flow that includes particulates of a desired size range that are directed onto an collection surface 534. Virtual impactor 532 can be one of the virtual impactors described above, although it is also contemplated that other designs of virtual impactors might also be used. A fluid is forced into virtual impactor 532 by fan 533, and as described above, that fluid is separated into both a major flow and a minor flow. The major flow is directed to exhaust 535, while the minor flow is directed to an collection surface 534.

Collection surface 534 can incorporate any of the coatings discussed above, or no coating. The configuration of collection surface 534 can include, but is not limited to, a plate, a disk, or an elongate tape. Preferably, collection surface 534 can be readily removed and replaced with a new collection surface either when the original collection surface is full, or particulates deposited on the collection surface require analysis.

Means 546 is employed to remove particulates collected on surface 534, and to transfer those particulates to a sample container 547. Specific examples of means 546 are described in greater detail below. Means 546 is operatively coupled to a control 538, which is also discussed in greater detail below.

Preferably, collection surface 534 is coupled to a prime mover 536 that moves the collection surface relative to virtual impactor 532 over time, so that particulates collected at different times are deposited on different portions of collection surface 534. It should be noted that prime mover 536 can instead optionally move virtual impactor 532, instead of, or in addition to, moving collection surface 534. It should be recognized that such a feature represents an additional functionality that is not explicitly defined with respect to the air samplers of FIGS. 1A and 2. That is, it should be recognized that the incorporation of a prime mover configured to move at least one of the collection surface and a virtual impactor represents a concept that can optionally be incorporated into an air sampler consistent with FIGS. 1A and 2, but is not required. However, in a test system developed to test the concepts disclosed herein, a prime mover was configured to move an elongate tape based collection surface (see FIG. 10) relative to the concentrator component, to provide a fresh collection surface over time. That test system also incorporated a sampling component configured to remove a portion of the collection surface containing collected particles (using a punch, generally as described above in connection with FIG. 9C). The removed portion was then rinsed with a liquid to generate a liquid sample. Empirical tests indicated that about 70% of collected particles could be recovered in a liquid sample.

Referring once again to FIG. 9E, with respect to embodiments in which prime mover 536 is drivingly coupled to collection surface 534; several different types of motion are contemplated. If collection surface 534 is a disk, prime mover 536 will likely be used to rotate the disk. If collection surface 534 is an elongate tape, then prime mover 536 will likely be used to cause one or both of a take-up wheel or a drive wheel (not shown) to be moved, to cause a corresponding movement in the elongate tape. It is contemplated that collection surface 534 will be a consumable component, which when full, will be replaced with a fresh collection surface.

Prime mover 536 is controllably coupled to a control 538. The purpose of control 538 is to control the movement of prime mover 536 to achieve the desired movement of either virtual impactor 532 or collection surface 534, and to actuate means 546 when a sample of particulates is to be transferred from surface 534 to container 547. Means 546 can be actuated based on the occurrence of a predefined condition (such as a sensor indicating that a triggering event has occurred), based on an affirmative user command, or according to a predefined sampling protocol. For example, an integrated system can be designed to deposit a plurality of spots during a given time period, where some of the spots are to remain on the collection surface, and others of the spots are to be transferred to a sample container.

It is contemplated that control 538 can be one of a computing device, an application specific integrated circuit (ASIC), a hardwired logic circuit, or a simple timing circuit. In at least one exemplary embodiment, software is executed to control the operation of the device, and the control includes a memory and a microprocessor. This software can include a program that determines the positioning of the collection surface relative to the minor flow. The software may also include a program that controls the schedule for taking environmental samples at predetermined times, thereby producing a spot on the surface at specific spaced-apart times. In addition, the air samplers disclosed herein may execute logic that modifies the sampling schedule in accordance with algorithms that are responsive to onboard sensors 540. Finally, the software can monitor the particulate collection, generating a log of the actual time when each sample is taken in association with the disposition of the spot deposited on an collection surface at that time. This log facilitates correlating a specific sample (i.e., a specific spot) with a particular moment in time at which the spot was deposited. Control 538 is shown as being controllably coupled to fan 533. According to one sampling protocol, fan 533 will operate continuously. According to another sampling protocol, fan 533 will operate for a predefined period of time while a spot is being deposited on the collection surface, and then will be de-energized by the control. The flow of fluid into the system can be interrupted between the deposition of samples that are deposited as spots, and when the collection surface is being replaced. It should be recognized that control 538 can be configured to implement a variety of different sampling and collection paradigms.

Empirical tests of a prototype device, functionally similar to system 530, and employing a polymeric tape as a collection surface, have confirmed the ability of a virtual impactor to deposit spots of particulates on a movable collection surface.

As noted above, in some embodiments, system 530 may beneficially include sensors 540, which communicate with control 538 to cause a sample to be collected in response to an event that is detected by the sensors (i.e., one or more sensors). For example, a collection system may be mounted in a smokestack of a manufacturing facility, to generate a collection record of emissions from the smokestack. Such a system might be equipped with a carbon monoxide monitor, and when levels of carbon monoxide are at a predetermined level (based on sensor data from sensors 540), controller 538 can be programmed to initiate a sampling event, to deposit particulates on the collection surface for later analysis in response to the sensor readings. Sensors can be used to measure relevant environmental factors that include, but are not limited to: pressure, humidity, temperature, particulate count, and the presence of a particular target bio-molecules (such as particular cell types, pathogens, and toxins). Based on the detection of a specific environmental factor by such a sensor, or in accord with a sampling protocol programmed into control 538, one or more of the following exemplary functions (as well as many others) can be executed by control 538: generate a record of the environmental conditions at the time of spotting; control the operation of any system component whose performance depends on a measured environmental parameters; manipulate a programmed sampling protocol based on measured environmental factors; actuate means 546 to transfer collected particulates to a sample container; and produce an alert signal (for example, by a radio transmission or a hard-wired signal transmission) to notify an operator of an important change in the environmental conditions (as determined by programmed control parameters).

Referring once again to FIG. 9E, a timer 542 is optionally included to provide a timing signal to control 538. Depending on the type of computing device (or logic circuit) employed for control 538, timer 542 may not be required. Many computing devices employ an internal clock that can be used for determining the passage of time and do not require a separate timer, and in its simplest form, control 538 may itself comprise a timer or be an integrated circuit that is designed to provide a timer function.

One or more optional detectors 544 can be included to analyze particulates deposited on the collection surface. It is expected, however, that the collection surface will most often be removed from the system before any of the particulates (i.e., spots) are analyzed. By using a separate detector, the cost of system 530 can be reduced, since detectors are often sophisticated and expensive. Furthermore, many detection methods require particulates comprising the spots to be removed from the collection surface before being analyzed. If detector 544 requires the particulates comprising the spots to be removed from the collection surface prior to their analysis, a particulate removal system (generally a liquid rinse directed at a specific spot) must also be incorporated. Particulates comprising the spots can also be removed by scraping, and with other means.

Preferably system 530 will often be used in a fixed (permanent) location to monitor a specific geographical location over a long period of time. Spent collection surfaces will be removed for storage and or analysis, and new collection surfaces can then be inserted into system 530. It is contemplated that system 530 can also be used as a survey instrument that is likely to be moved from one location to another, to collect samples at different geographic locations. Such a survey instrument can be used to obtain samples (spots) from many locations within a region (or at different regions) on a single collection surface. This feature has utility in determining the source of a particular contaminant and monitoring a number of locations when the spots on the collection surface are subsequently analyzed, although it should be recognized that an analytical component that is used with a system including the various samplers disclosed above, can be beneficially implemented in system 530 as desired.

While not specifically shown, it is further contemplated that system 530 can beneficially have the ability to communicate with a control system at a remote location, to send and receive control signals and communicate other data.

In many applications, it may be important that the system be able to sample a large volume of air ($\geqq 300$ lpm), but that the sample collected be deposited in a small area (e.g., as spots ~1 mm in diameter). To achieve these goals, it will be important to achieve the separation of particulates from a large air volume and their concentration in a relatively smaller air volume (i.e., the minor flow). In such applications, it is contemplated that two in-line stages of virtual impaction may be used. In the first stage, 90% of the inlet fluid is discarded, and the remaining 10% of the fluid (first stage minor flow) contains the desired particles. This first stage minor flow then enters a second virtual impactor stage, with 90% of fluid that enters the second stage being exhausted to the environment. Therefore, the two stages have the combined effect of concentrating the outlet minor fluid volume to $\frac{1}{100}^{th}$ of the initial inlet flow volume. This relatively small minor flow should then be appropriate for depositing the concentration of particulates as spots onto a small surface area. The spot density on the surface should typically be as high as possible, without cross-sample contamination occurring, in order to minimize the required area of the collection surface.

Means for Transferring Particles from a Collection Surface to a Container: In several embodiments of the air samplers disclosed herein, a fluid is used to remove and transfer the particulates from the collection surface to a container. Depending upon the collector employed, the fluid can be a liquid or a gas. FIG. 10 schematically illustrates a particle impact collector 625 that includes tape 620' having coated impact collection surface 623, preferably enclosed in a housing 652. As noted above, an integrated system made in accord with the concepts disclosed herein can also include means for transferring collected particulates to a container. Tape 620' advances from a supply reel 624 onto a take-up reel 626, as indicated by a directional arrow 622. An electric motor 640 coupled to take-up reel 626 rotates the take-up reel at a selected speed so that the tape passes under stream 621 of fluid 610. Particulates 614 impact on the coated impact collection surface of the tape and are carried toward the take-up reel by the moving tape.

Other elements of particle impact collector 625 include a fan 628, which is rotatably driven by an electric motor 630. Fan 628 impels fluid 610 in stream 621 toward coated impact collection surface 623. Other types of fans or impellers can alternatively be used. For example, a centrifugal fan (not shown) can be employed to move the fluid. If the fluid in which the particulates are entrained is a liquid, a pump (not shown) would be used instead of fan 628 to move fluid 610 toward coated impact collection surface 623.

To obtain a concentrated sample of particulates 614 from those collected on coated impact collection surface 623*a*, particle impact collector 625 preferably includes a specimen container 636 that is filled with a collected sample through a funnel 634. A liquid 638 that is rich in the particulates collected on the coated impact collection surface partially fills sample container 636. Liquid 638 is obtained by washing the particulates from the tape. A reservoir 642 is included to supply the liquid for this purpose. The liquid from the reservoir is conveyed through a fluid line 644 and sprayed toward tape 610 through a nozzle 646, which creates a fan-shaped spray 648 that washes the particulates from the tape. If necessary, a pump, e.g., a centrifugal or a peristaltic pump (not shown) may be used to force the liquid through nozzle 646 under sufficient pressure to wash away the particulates retained by the coated impact collection surface. These particulates are carried by a stream 650 of the liquid into funnel 634 and thus are conveyed into sample container 636. A relatively small volume of liquid can be employed, so as to avoid unnecessarily diluting the sample.

The material used for producing coated impact collection surface 623 and other coated areas or surfaces employed in other embodiments discussed herein for collecting particulates in accord with the concepts disclosed herein, is selected because of certain characteristics of the material that increase the efficiency with which the particulates are separated from the fluid in which they are entrained, and to enhance the removal of the particulates so that they may be transferred to a sample container. Each material used for a coating has certain advantages that may make it useful for separating a specific type of particulate from a specific type of fluid. For example, for use in particle impact collector 625, the TETRAGLYME material described above can be used for the coating. As noted above, this material is hydrophilic until it is exposed to water, and when dry, is relatively tacky, tending to readily retain particulates that impact it. Once water is sprayed onto the TETRAGLYME coated surface, the particulates that have been retained on the surface are readily released.

It should be recognized that collection/deposition substrate 623 is moved relative to the concentrated stream of particulates from the impactor over time, so that spots or samples of the particulates that have been collected on different portions of the collection/deposition substrate 623 correspond to different times at which the particulates were collected. Because the location of a "spot" of particulates deposited on the sample substrate (or collection/deposition substrate) is indicative of a time when the particulates were collected, the substrate can be made to move relative to the impactor, at least at spaced-apart times, to form spots of particulates (or continually, to form streaks of particulates). Moving the substrate at successive specific times permits multiple sample spots to be deposited on a single substrate without commingling the spots. The time at which each spot is deposited is associated with the spot. Alternatively, time can be linear in its association with a position of a particle as part of a streak of particles that are deposited continuously.

FIGS. 11A and 11B illustrate a fluid jet directed onto a collection surface, which may or may not be coated. The fluid may be a liquid (such as water) or a gas (such as air). Note that the difference between a liquid rinse and a gaseous jet is that the gaseous jet has significantly more kinetic energy than a liquid rinse. In a liquid rinse, the liquid is just acting as a carrier, picking particles up from the collection surface and rinsing them away. In contrast, with use of a gaseous jet having substantially greater kinetic energy, there is a real mechanical action, in which heat and friction created by the impinging high-velocity gas stream facilitate detachment of the particles from the surface. In a sense, the liquid rinse relies primarily on reduction of surface tension, and to a lesser extent, on the solvent power of the rinse liquid. The gaseous jet essentially "blasts" the particles off the collection surface and into a sample container.

FIG. 11A illustrates the use of a gaseous jet 718 to remove particles 714 from collection surface 716, and to transfer those particles into a sample container 720. Note that how the particles are deposited on the collection surface is not important in this Figure, since the Figure simply illustrates one way in which such particles can be transferred to a sample container after they are collected. Source 712 of gaseous jet 718 may be directional, so that the gaseous jet is able to be directed at a particular deposit of particles on collection surface 716. It is also contemplated that source 712 can instead be fixed in position, and that collection surface 716 can instead be moved relative to the fixed source to selectively impinge the gaseous jet on a particular group of particles.

The integrated system embodiment of the concepts disclosed herein that are discussed above provide details indicating how a collection surface can be moved. It may generally be preferable that source 712 and the inlet used for directing particles toward the collection surface for collection not be disposed in substantially the same position. However, if both the inlet and source 712 are not operated simultaneously, such a configuration should not be a problem.

The fluid jet is directed at a selected group (or spot) of particles, which are "blasted" off the collection surface and into container 720. Container 720 should be properly positioned so that substantially all of the particles blasted from the collection surface are directed into the container. If desired, container 720 can be coupled in fluid communication with a vacuum source 722, so that particles are affirmatively drawn into container 720. Such a configuration reduces the likelihood of particles being dispersed in directions other than toward the sample container. Of course, a suitable filter must be employed to prevent the particles from escaping container 720 through the line that couples the vacuum source to the container. The angle at which fluid jet 718 is directed toward the collection surface should be selected to direct the blasted particles into the collection container.

When fluid jet 718 comprises a gas, the particles are transferred into the sample container without the use of any liquid, and no dilution of the sample has taken place. A further benefit of using a gas for the jet is that container 720 can be sealed and stored dry, so that a liquid is added only immediately before analysis of the sample stored in the sample container. This approach also reduces the weight of the sample, which can be important, particularly in an integrated system embodiment in which many samples are taken, since use of dry samples can significantly reduce the total weight of the samples. The gas selected for the fluid jet should be inert with respect to the particles collected, so that no undesired reactions occur between the sample particles and the gas. Preferred gases include compressed air, compressed nitrogen, compressed carbon dioxide, and inert gases such as argon.

When fluid jet 718 comprises a liquid, care should be taken not to use too much liquid, so that the sample of particles are not unduly diluted. Because of the energetic nature of the fluid jet, even a small amount of liquid is expected to be effective in transferring the particles from the collection surface and into the sample container.

FIG. 11B illustrates an embodiment in which the collection surface can be rotated by 90 degrees, so that source 712 can be disposed above particles 714, while container 720 is disposed below the particles. Fluid jet 718 is applied to cause the particles to fall or be forced directly into container 720. Once the particles are collected, the collection surface can be rotated by 90 degrees such that collection surface 716 is properly positioned to collect particles moving in the same direction as fluid jet 718. It should also be understood that the fluid stream into which the particles are originally entrained could be directed toward an impact collection surface that is not oriented horizontally, such that particles impact on an upper portion, but instead, is oriented vertically, so that particles impact a side surface. In such a vertical orientation, the collection surface would not need to be rotated by 90 degrees to enable the transfer of particles into a sample container, as shown in FIG. 11B. As noted above, container 720 can be placed in fluid communication with a vacuum (pump or source) 722.

A mechanical scraper 724 can be employed to remove and transfer selected particles 714 to container 720, as shown in the end view of FIG. 12A and plan view of FIG. 12B. A small volume of liquid can also be employed to rinse scraper 724, as shown in FIG. 13. As discussed above, the use of too much liquid should be avoided. Note that if scraper 724 is placed into container 720, then a gas jet can be employed to direct the particles into the container, enabling a dry sample to be collected. Particularly when container 720 is coupled in fluid communication with a vacuum, and a filter or trap is employed to prevent the particles from escaping the container, the use of a gas jet is not likely to result in dispersing the particles in undesired directions, so that they are lost into the environment.

Another method of removing particles from scraper 724 without the use of a liquid rinse is to place the scraper in or immediately adjacent to container 720, and then to rapidly vibrate scraper 724, as is shown in FIG. 14. The vibrating action will tend to disperse any particles clinging to the scraper, and such particles will then fall into or otherwise be collected within the container. As noted above, container 720 can be placed in fluid communication with a vacuum (pump or source) 722. Note that instead of, or in addition to vibrating scraper 724, the container itself can be vibrated. When container 720 contains a liquid, the vibrations will enhance the removal of particulates from the scraper.

Instead of removing the particles from the collection surface, in some embodiments, the portion of the collection surface containing a specific spot of particulates is removed and placed into a container. In a first such exemplary embodiment, shown in FIG. 15A, collection surface 716*a* is pre-scored into individual sections 728, enabling sections of the collection surface to be easily removed. The pre-scored sections can be larger than the spot sizes, and smaller than the container. The pre-scored section is simply removed and placed in the container. No liquid is required, and the sample can be stored dry. Of course, the container can be filled with a desired quantity of liquid after, or even before, the portion of the surface is placed into the container. A punch 730 with a raised inner portion 732 enables the pre-scored portion to be removed without dislodging any of the particulates. In one exemplary embodiment, the punch can be disposed above the surface, and the container below the collection surface. Either the collection surface, or the container and punch can be repositioned to select a desired portion of the collection surface to remove.

If the collection surface is easily cut (such as a thin fiber or plastic material), then pre-scoring may not be required. Particularly if the outer periphery of the punch is sharp, the punch will be able to remove un-scored portions of such a thin collection surface. The punch, or other member used to remove a portion of the collection surface, should not disturb the spot of particles on the collection surface.

The "punched" portion of the collection surface will fall into the container due to gravity. However, it may be useful for the container to be in fluid communication with a vacuum source as described above, to draw the removed portion into the container. A fluid jet 718 (preferably air) can be directed toward the cut portion of the collection surface to drive that portion into the container; however, such a jet has the potential to direct the particles in the spot in undesired directions (i.e., away from, rather than into, the container).

Note that a collection surface can be fabricated from a soluble material, such as starches or gelatin. When a portion of such a surface is placed into a container and a suitable liquid is added, the collection surface will dissolve, enabling the particles to freely disperse within the sample container. This technique can be quite beneficial, particularly in cases in which the presence of a portion of a collection surface in a liquid sample is not compatible with a particular analytical method.

It is contemplated that combinations of the above techniques can be useful. For example, a collection surface can be coated with a dissolvable coating, so that when a liquid jet is directed at that portion of the collection surface (see FIGS. 11A and 11B), the coating is dissolved, and particles are readily removed. Another variation is to use a pre-scored collection surface coated with a dissolvable coating. After the pre-scored portion is placed in a container, and a liquid has been added to the container to dissolve the coating, the remaining portion of the collection surface can then be removed from the container.

Yet another variation, shown in FIG. 15B, is to employ a pre-scored collection surface 716*b* with a plurality of surface indentations 734. The particles are directed into the indentations, and then a normal punch 736 can be employed to remove the scored portions without disturbing the particles disposed in the indentation.

Suitable sample containers can be made of plastic, although glass, metal, and ceramic can alternatively be employed. As with any sample container used to collect a sample for analysis, containers should be inert and clean, so that contaminants are not introduced into the sample.

FIGS. 9A-9E, 10, 11A, 11B, 12A, 12B, 13, 14, 15A, and 15B generally relate to removing particles from a collection surface to obtain a liquid sample. In contrast, exemplary air sampler 10*c* of FIG. 16 is specifically configured to generate a gaseous or vaporous sample 23 and can be used when the analytical component requires such a sample. Air sampler 10*c* of FIG. 16 is very similar to air sampler 10*b* of FIG. 2, except that collection surface 46*a* (which replaces collection surface 46 of FIG. 2) is configured to be coupled in fluid communication with chemical sensor 22*a* (which replaces analytical component 22 of FIG. 2), and heat source 20*a* (which replaces sampling component 20 of FIG. 2) is configured to heat at least a portion of collection surface 46*a*, to vaporize at least some particulates, producing a vaporized sample 23 that is conveyed to chemical sensor 22*a* for analysis. A fan 25 has been added to draw vaporized sample 23 from collection surface 46*a* to chemical sensor 22*a*, (although it should be recognized that one of the other fans in air sampler 10*c* could be used for this purpose). Heat source 20*a* can be implemented as a laser, an IR heat lamp, an electrical resistive heater, or other type of heater. It should also be recognized that a heat source for vaporizing a sample can be added to embodiments that collect a liquid sample, where the heat source heats the liquid sample to vaporize the liquid sample, thereby generating a vaporous or gaseous sample. Suitable hose, tubing or other conduits can be used to convey the gaseous sample from the collection surface (or container holding a liquid sample) to the chemical sensor. It should be noted that the heat source can be configured to heat the collection surface not only to generate a gaseous or vaporous sample, but also to regenerate the collection surface, such that previously collected particles are removed and cannot contaminate samples comprising particles collected after regenerating the collection surface.

FIG. 17 schematically illustrates an air sampler incorporating an analytical component and a collection surface regenerating component, but which does not require a sampling component, because the sample is analyzed optically while on the collection surface. It should be recognized that the collection surface regenerating component described in conjunction with FIG. 17 can also be beneficially incorporated into any of the other air samplers disclosed herein. The exemplary optical biological particle detection system of FIG. 17 includes an impaction plate 205 (i.e., a sample substrate) with a collection surface on which a deposit or spot 220 of particles is formed, a spotting nozzle 210 (the spotting nozzle can be part of or coupled in fluid communication with a virtual impactor, generally as discussed above), an optical biological detector 230 (configured to detect biological particles, for example, by stimulating fluorescence of naturally occurring proteins such as NADH and tryptophan), at least one excitation light source 240 (coupled by wires 250 to a power supply that is not separately shown, the light source inducing the fluorescent phenomenon detected by detector 230), a shaft 260 drivingly coupled to impaction plate 205 by a bracket 270, and a regenerator 280. Three collection surfaces/spots are indicated in FIG. 17, for illustration only, since a single collection surface generally suffices in most applications. The shaft is drivingly coupled to a prime mover (not separately shown), and detector 230 can be coupled to a computing device/processor (also not separately shown) by wires 250.

As noted above, the spotting nozzle directs a jet of gaseous fluid toward the impaction plate. The spotting nozzle (i.e., the acceleration nozzle) may be of various shapes, such as round or configured as a slit. A round acceleration nozzle includes a generally round outlet through which the gaseous fluid is directed. The nozzle body may be generally cylindrical. A slit-shaped acceleration nozzle includes a generally rectangular outlet through which the gaseous fluid is directed.

The impaction plate may take a variety of shapes, but the collection surface is typically flat. In some embodiments, the impaction plate is a disk, e.g., configured to be flat, thin, and circular. A disk axis extends perpendicularly through the center of the two generally parallel, circular shaped opposite surfaces of the disk. In such embodiments, the collection surface is on one of the two planar generally parallel surfaces of the disk, and can be spaced apart from the center (or from the disk axis).

The impaction plate can be made of a substantially homogenous material, although it is possible to embed or otherwise incorporate a collection surface of one material on an impaction plate made of a different material. The plate, or at least its collection surface, can be made of a material sufficiently durable to withstand repeated surface regeneration without incurring damage. Many materials are suitable for this purpose, including glass, quartz, ceramic, silicon, metal, and plastic. In addition, coatings used to increase the hardness and/or the resistance to abrasion of the material can be deposited on the material.

When detector 230 and light source 240 are disposed on opposite sides of the impaction plate, it should be recognized that the impaction plate (or at least that portion of the impaction plate where the nozzle deposits a spot of particles) should be formed of an optically transparent substrate. Exemplary optically transparent substrates comprise UV transparent materials such as fused silica, pure silica, and sapphire (available from Edmond Scientific Co.). However, when detector 230 and light source 240 are disposed such that light from the light source can reach the deposited particles, and light from the deposited particles can reach the detector without interference from the impaction plate, impaction plates comprising non-optically transparent substrates can be employed.

In an exemplary embodiment, the collection surface is substantially smooth. A smooth surface may be preferred since it can more readily be cleaned by the surface regenerator. On the other hand, particles tend to bounce off smooth surfaces more easily, thus decreasing collection efficiency. Consequently, in some embodiments, the collection surface has outwardly projecting structures, such as rods or ribs. For example, the collection surface can be micro-machined to incorporate pyramid-shaped structures of approximately 1 μm-10 μm in height and width. In these embodiments, particle loss is minimized, but relatively harsher surface regenerators are required for cleaning the collection surface.

One function of the impaction plate is to support the collection surface for the accumulation of a sample of airborne particles during impaction. Accordingly, at least at one point in the cycle of operation of the device, the collection surface is disposed adjacent to the spotting nozzle. Typically, the collection surface is horizontal while the spotting nozzle is vertical.

The surface regenerator is configured to regenerate the surface, i.e., to remove a spot or deposit of particles from the collection surface after analysis, and thus, to make the collection surface available for collecting another spot. The surface regenerator must remove substantially all of the spots from the collection surface, so that a prior use of the collection surface does not contaminate or otherwise interfere with analysis of samples comprising subsequently gathered spots.

In some embodiments, especially where a smooth collection surface is employed, a surface regenerator may comprise a felt or cloth pad that is pressed against a moving collection surface as it slides towards the nozzle. The term "felt" is intended to generally encompass any form of a porous fibrous structure, typically unwoven, created by interlocking fibers using heat, moisture, or pressure. Suitable fibers include, but are not limited to, polyester, polyurethane, polypropylene, and other synthetic and natural fibers. The term "cloth" is intended to convey a material that is made by weaving, felting, knitting, knotting, or bonding natural or synthetic fibers or filaments. Of course, movement of a pad relative to the collection surface while a force is applied may be achieved by many different means. Alternatively, a felt or cloth wheel may be employed, wherein a motor spins the wheel when it is in contact with the spot, thus cleaning and regenerating the collection surface. In other embodiments, the surface regenerator can be configured as a brush or blade that removes the spot, with a sweeping or scraping motion. When the collection surface is not smooth, one or more brushes are desirable, and their sweeping motion may be performed in multiple directions. In yet other embodiments, surface regeneration can be achieved by blowing a stream of fluid (such as air or a rinse liquid) at an angle toward the spot, i.e., the surface regenerator comprises a nozzle oriented an angle towards the collection surface, which blows a stream of fluid at high velocity towards the collection surface. In some embodiments, regeneration is aided by electro-statically charging the spot either before or during the action of the regenerator. The collection surface may be temporarily provided a positive charge, a negative charge, or alternating positive and negative charges. In some embodiments, the regenerator comprises at least in part, heaters or lasers capable of transferring energy to and heating the surface spot/collection surface. In some embodiments, multiple regenerators are included and are used sequentially in each cycle of the device, or periodically (i.e., a normal cleaning after each collection cycle, followed by periodic deep cleanings after each of a predefined number of collection cycles).

Some embodiments incorporate an optional size selective inlet 290 for preconditioning the air sample (i.e., the gaseous fluid) by removing particles above a desirable size (this element is generally consistent with the pre-filter discussed above in detail). A "size-selective inlet" removes particles above a certain size (aerodynamic diameter) from a stream or sample of gas. The term "remove" is intended to mean that for a predetermined particle size, about 50% of the particles are removed from the gas sample, and the remaining particles pass through the size-selective inlet. For particles of smaller sizes than the predetermined size, most, or almost all, particles pass through the inlet, while for particles of sizes larger than the predetermined size, most, or almost all, particles are removed. The substrate of a size-selective inlet collects the removed particles. In certain embodiments, a size-selective inlet comprises an inertial impactor. The size of the particles removed is determined, in part, by the velocity of the gas sample as it comes out of the acceleration nozzle. The higher the velocity, the smaller the size of the particles removed. Thus, by selecting the appropriate acceleration nozzle, a predetermined upper size of particles can be removed from a gas sample. In certain embodiments, a size-selective inlet can comprise a filter, an elutriator, or any other device capable of removing particles greater than a predetermined size. In at least one embodiment, the size-selective inlet removes particles above about 10 μm, but may be set to remove particles above other different sizes, for example, above about 12 μm, above about 15 μm, above about 20 μm, and above about 25 μm. In those embodiments where a virtual impactor is included, the size-selective inlet may be disposed either upstream or downstream of the virtual impactor. Removal of large airborne particles eliminates potential sources of interference with the optical detectors discussed above.

One exemplary embodiment providing for intermittent relative motion between the sample substrate and the adjacent stream of particulates is shown in FIG. 18, in which an impactor 510 is fixedly mounted over a movable sample substrate that is formed in the shape of a disk 516. The impactor inlet flow is directed at the disk. The impactor exit flow 512 containing particulates of non-target size exits impactor 510 orthogonally with respect to the impactor inlet flow.

The nozzle directing the minor flow from the impactor toward disk 516 cannot be seen in FIG. 18, but virtual impactor 510 includes at least one minor flow outlet, oriented to direct particulates towards spot deposition areas 514*a*. As disk 516 rotates beneath virtual impactor 510, the minor flow nozzle of virtual impactor 510 directs particulates to a new deposition area. Note that disk 516 has a circular ring of spaced-apart deposition areas 514*a*. Disk 516 can be indexed (not shown) so that the spots are defined at discrete predetermined positions around the ring in the deposition areas, which enables the position of each spot to be associated with a specific time, and enables the particulates to be accurately directed toward the disposition at each spot on the disk. It should be understood from FIG. 18 that deposition area 514*a* can include a plurality of depressions formed into disk 516, either as openings in a coating on disk 516, or as depressions formed into the surface of disk 516, disposed where each spot of particulates is to be deposited. However, while such openings/depressions are expected to increase collection efficiency, they are not required.

Disk 516 can be moved using an appropriate prime mover 520, such as a stepper motor. As shown, one embodiment includes a shaft 518 detachably coupled to disk 516 and driven by prime mover 520. It is contemplated that disk 516 will remain stationary for a desired time interval, and then will be rotated a sufficient amount to collect another distinct spot on the disk. The impactor can be cycled off during the movement if desired.

In another embodiment, the sample substrate (e.g., the disk) is continually moved at a fixed rate, resulting in annular rings defined by streaks of particles on the sample substrate, instead of discrete spots. The use of streaks somewhat simplifies the operation of the collector, in that it can operate continuously, rather than being cycled on and off.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for collecting a sample of particulates entrained in a flow of fluid, comprising the steps of:
    (a) separating the fluid flow into a major flow and a minor flow, the major flow including a minor portion of particulates above a first predetermined size and the minor flow including a major portion of the particulates above the first predetermined size, the separation being performed using virtual impaction;
    (b) directing the minor flow onto a collection surface disposed within a housing of a sample device, such that particulates entrained in the minor flow are deposited on the collection surface, the deposition being performed using actual impaction; and
    (c) removing a portion of the particulates deposited on the collection surface to obtain a sample of the particulates, without removing the collection surface from the sample device in which the collection surface is disposed to collect the deposited particulates; and
    (d) regenerating the collection surface after the step of removing the portion of particulates to obtain the sample, such that particulates deposited on the collection surface prior to the step of regenerating the collection surface do not contaminate subsequent samples.

2. The method of claim 1, wherein the step of removing the portion of the particulates comprises the step of heating the collection surface to obtain a gaseous sample.

3. The method of claim 1, further comprising the step of analyzing the sample of particulates, without removing the sample from the sample device.

4. The method of claim 1, wherein the step of directing the minor flow onto the collection surface comprises the step of directing the minor flow through a bed comprising a plurality of beads, the beads being substantially larger than the particulates being collected, the collection surface comprising the surfaces of the beads.

5. The method of claim 1, wherein the step of directing the minor flow onto a collection surface comprises the step of directing the minor flow onto a coating on the collection surface, wherein the coating on the collection surface comprises at least one material selected from the group consisting of:

(a) a material characterized by its ability to retain particulates impacting thereon when dry, and having a relatively low coefficient of adhesion when wetted, so that the particulates that have impacted on the collection surface and been retained thereon are readily washed from said surface with a liquid;

(b) a material that attracts substantially only biologic particulates of a specific desired type, for efficiently separating said particulates from the minor flow of fluid, said coating binding with the particulates of the specific desired type to retain them on the collection surface; and (c) a material that changes state while being retained on the collection surface, a first state of the material being characterized by its ability to retain the particulates that impact thereon, separating the particulates from the minor flow of fluid, and a second state of the material being characterized by its ability to readily release the particulates separated from the minor flow of fluid.

6. The method of claim 1, further comprising the step of filtering the fluid before the step of separating the fluid flow into the major flow and the minor flow, to substantially remove particulates larger than a second predetermined size.

7. The method of claim 6, wherein the step of filtering the fluid before the step of separating the fluid flow into the major flow and the minor flow comprises at least one step selected from the group of steps that include:

(a) filtering the fluid using an impactor; and (b) filtering the fluid using a filter comprising a plurality of pores smaller than the second predetermined size.

8. The method of claim 6, wherein the step of filtering the fluid before the step of separating the fluid flow into a major flow and a minor flow comprises the step of filtering the fluid using a virtual impactor.

9. The method of claim 1, wherein the step of regenerating the collection surface comprises the step of regenerating the collection surface without removing the collection surface from the sample device.

10. The method of claim 1, wherein the step of regenerating the collection surface comprises at least one step selected from the group of steps including:

(a) wiping the collection surface with a cleaning pad;

(b) cleaning the collection surface using a plurality of bristles;

(c) heating the collection surface to a pre-defined temperature; and (d) rinsing the collection surface with a solvent.

11. A method for collecting a sample of particulates entrained in a flow of fluid, comprising the steps of:

(a) separating the fluid flow into a major flow and a minor flow, the major flow including a minor portion of particulates above a first predetermined size and the minor flow including a major portion of the particulates above the first predetermined size, the separation being performed using virtual impaction;

(b) directing the minor flow onto a collection surface disposed within a housing of a sample device, such that particulates entrained in the minor flow are deposited on the collection surface, the deposition being performed using actual impaction; and (c) optically analyzing the particulates deposited on the collection surface, without removing the collection surface from the sample device in which the collection surface is disposed; and (d) regenerating the collection surface after optically analyzing the particulates deposited on the collection surface, such that particulates deposited on the collection surface prior to the step of regenerating the collection surface do not contaminate subsequently deposited samples of particulates.

12. The method of claim 11, wherein the step of directing the minor flow onto a collection surface comprises the step of directing the minor flow onto a coating on the collection surface, wherein the coating on the collection surface comprises at least one material selected from the group consisting of:

(a) a material characterized by its ability to retain particulates impacting thereon when dry, and having a relatively low coefficient of adhesion when wetted, so that the particulates that have impacted on the collection surface and been retained thereon are readily washed from said surface with a liquid;

(b) a material that attracts substantially only biologic particulates of a specific desired type, for efficiently separating said particulates from the minor flow of fluid, said coating binding with the particulates of the specific desired type to retain them on the collection surface; and (c) a material that changes state while being retained on the collection surface, a first state of the material being characterized by its ability to retain the particulates that impact thereon, separating the particulates from the minor flow of fluid, and a second state of the material being characterized by its ability to readily release the particulates separated from the minor flow of fluid.

13. The method of claim 11, further comprising the step of filtering the fluid before the step of separating the fluid flow into the major flow and the minor flow, to substantially remove particulates larger than a second predetermined size.

14. The method of claim 13, wherein the step of filtering the fluid before the step of separating the fluid flow into the major flow and the minor flow comprises at least one step selected from the group of steps that include:

(a) filtering the fluid using an impactor; and (b) filtering the fluid using a filter comprising a plurality of pores smaller than the second predetermined size.

15. The method of claim 13, wherein the step of filtering the fluid before the step of separating the fluid flow into a major flow and a minor flow comprises the step of filtering the fluid using a virtual impactor.

16. The method of claim 11, wherein the step of regenerating the collection surface comprises the step of regenerating the collection surface without removing the collection surface from the sample device.

17. The method of claim 11, wherein the step of regenerating the collection surface comprises at least one step selected from the group of steps including:

(a) wiping the collection surface with a cleaning pad;

(b) cleaning the collection surface using a plurality of bristles;

(c) heating the collection surface to a pre-defined temperature; and (d) rinsing the collection surface with a solvent.

* * * * *